(12) United States Patent
Ward et al.

(10) Patent No.: US 11,674,131 B2
(45) Date of Patent: Jun. 13, 2023

(54) INDIRECT ULTRASONIC CAVITATION-DERIVED PERIVASCULAR CELLS AND METHODS OF USE THEREOF

(71) Applicants: Ross Ward, Hattiesburg, MS (US); Jory Scott, Laurel, MS (US)

(72) Inventors: Ross Ward, Hattiesburg, MS (US); Jory Scott, Laurel, MS (US)

( * ) Notice: Subject to any disclaimer, the term of this patent is extended or adjusted under 35 U.S.C. 154(b) by 391 days.

(21) Appl. No.: 16/700,533

(22) Filed: Dec. 2, 2019

(65) Prior Publication Data
US 2020/0172894 A1    Jun. 4, 2020

Related U.S. Application Data

(60) Provisional application No. 62/774,835, filed on Dec. 3, 2018.

(51) Int. Cl.
| | | |
|---|---|---|
| C12N 13/00 | (2006.01) | |
| C12N 5/071 | (2010.01) | |
| C12N 5/0781 | (2010.01) | |
| C12N 5/0783 | (2010.01) | |
| C12N 5/0787 | (2010.01) | |
| C12N 5/078 | (2010.01) | |
| C12N 5/0786 | (2010.01) | |
| C12N 5/0789 | (2010.01) | |
| A61K 35/44 | (2015.01) | |

(52) U.S. Cl.
CPC .............. *C12N 13/00* (2013.01); *A61K 35/44* (2013.01); *C12N 5/0691* (2013.01); *C12N 5/0635* (2013.01); *C12N 5/0637* (2013.01); *C12N 5/0642* (2013.01); *C12N 5/0644* (2013.01); *C12N 5/0645* (2013.01); *C12N 5/0647* (2013.01)

(58) Field of Classification Search
CPC .... C12N 13/00; C12N 5/0691; C12N 5/0635; C12N 5/0637; C12N 5/0642; C12N 5/0647; C12N 5/0645
See application file for complete search history.

(56) References Cited

FOREIGN PATENT DOCUMENTS

| WO | WO 2012/091911 A1 | 7/2012 | |
|---|---|---|---|
| WO | WO 2014/015229 | 1/2014 | |
| WO | WO 2014/138383 A1 | 9/2014 | |
| WO | WO 2014/152282 A1 | 9/2014 | |
| WO | WO-2014152282 A1 * | 9/2014 | ........... C12N 5/0667 |
| WO | WO 2014/179834 | 11/2014 | |

OTHER PUBLICATIONS

International Search Report dated Apr. 14, 2020, regarding PCT/US2019/063947.
Vezzani et al., "Higher Pericyte Content and Secretory Activity of Microfragmented Human Adipose Tissue Compared to Enzymatically Derived Stromal Vascular Fraction", Stem Cells Translational Medicine, 7:786-886, 2018.
Extended European Search Report issued in European Application No. 19893526.4, dated Mar. 8, 2022.

* cited by examiner

*Primary Examiner* — Kara D Johnson
(74) *Attorney, Agent, or Firm* — Parker Highlander PLLC

(57) ABSTRACT

The present invention is directed to indirect ultrasonic cavitation-derived perivascular cells, to methods of use of a perivascular cell composition, to a method of processing a tissue and to an apparatus for the processing of a tissue. The methods include the mechanic indirect ultrasonication of a cellular non-structural tissue, and produce a perivascular fraction which includes perivascular cells. The methods of use are directed to the treatment of a variety of diseases and disorders and to the improvement of a tissue in a subject. The apparatus is provided for the processing of cellular non-structural tissue.

10 Claims, 2 Drawing Sheets

INDIRECT ULTRASONIC CAVITATION-DERIVED PERIVASCULAR CELLS AND METHODS OF USE THEREOF

CROSS-REFERENCE TO RELATED APPLICATIONS

This application is based on and derives the benefit of the filing date of U.S. Provisional Patent Application No. 62/774,835, filed Dec. 3, 2019. The entire content of this application is herein incorporated by reference in its entirety.

BACKGROUND OF THE INVENTION

Field of the Invention

The present invention relates generally to perivascular cell isolation and to methods of use thereof, and more specifically to the use of indirect ultrasonic cavitation for the isolation of a perivascular fraction from cellular non-structural tissue.

Background Information

Historically, stem cells were derived from embryos, bone marrow aspirate and adipose tissue and used to treat a variety of disease states. Most of these therapies involve single infusion or injection of the stem cells. Perivascular fractions (PVF) contain a small percentage of stem cells. These cells in general support healing. Perivascular cells or pericyte vascular cells include a mixture of adipose and/or cellular non-structural tissue derived stem cells/mesenchymal stem cells, endothelial/progenitors, pericytes, fibroblasts and other cells. The treatment or processing of cellular non-structural tissue depends on the tissue from which the PVF is isolated, generally fat or adipose tissue derives.

Presently in order to produce pericyte vascular fraction from cellular non-structural tissue an enzyme such as collagenase is typically used. The collagenase dissolves the bonds in the collagen that hold together the tissue. Collagenases are endopeptidases that digest native collagen in the triple helix region. Collagens are the major fibrous component of animal extracellular connective tissue. Collagenases are present in different organisms including vertebrates and bacteria. Bacterial collagenases have a broad substrate specificity than vertebrate collagenases. In addition unlike bacterial derived collagenases split collagen into its native triple helix conformation. Bacterial collagenases are distinct in that they are capable of breaking down both water-insoluble native collagens and water-soluble denatured collagens. Bacterial collagenases is capable of breaking down almost all types of collagen and can effect multiple cleavages within the triple helical regions Conventionally collagenases are used to degrade collagens and separate the tissue into isolated cells, and work well for the purpose of obtaining PVF from a cellular non-structural tissue. However, the use of these enzymes may be disadvantageous for cellular products that are to be used in humans, e.g., cells or cell fractions which are to be used in tissue reconstruction or regeneration (breast reconstruction procedures, cosmetic skin rejuvenation or usage in cosmetic tissue fillers that are used during plastic surgery) because the use of this enzyme results in a "maximally manipulated" cellular product. However, the use of collagenase would potentially place PVF or perivascular cells (PVCs) derived from cellular non-structural tissue in a category that requires drug approval, even if the cell fraction is to be used cosmetically and not clinically.

Moreover, the use of enzymes such as collagenase results in higher rates of cell death, thereby reducing the number of the desired isolated cells, and further resulting in more cellular debris and in a less useful cell product, especially if the cells are to be used therapeutically. Accordingly, it would be desirable to provide alternative methods, e.g., mechanical methods, that produce PVF and PVCs suitable for administration to patients and that does not include collagenase.

The use of enzymatic techniques on structural tissues targets stem cells, and thus results in purified stem cell products. However, culturing, growing, and expanding techniques are then needed to increase the numbers of stem cells. Alternatively, mechanical techniques, such as direct sonic cavitation can also be used; however it damages the tissue by creating hotspots in the tissue.

Lately, the use of PVCs to treat a large number of diseases and disease states continues to grow more and more as research is performed, with patients receiving autologous PVCs (even though allogeneic PVCs infusions are possible, but not common). More efficient and non-damaging techniques to isolate PVCs are needed.

SUMMARY OF THE INVENTION

The present invention is based on the seminal discovery that perivascular cells (PVCs) can be isolated from perivascular fraction (PVF) obtained from cellular non-structural tissue by indirect sonication. Also provided are methods of treating cellular non-structural tissue using indirect ultrasonic cavitation to dissociate the pericytes and cells contained within cellular non-structural tissue and thereby obtaining pericyte or perivascular fractions for use in human subjects. These methods preferably do not include the use of any exogenous dissociating enzymes such as collagenase and result in increased numbers of PVCs (about 10-fold greater) than methods which use collagenase.

In one embodiment, the present invention provides a pericyte vascular fraction (PVF) composition including a PVF derived by a method including sonication of a cellular non-structural tissue; and a pharmaceutically acceptable carrier, diluent and/or excipient, wherein the sonication is indirect sonication.

In certain aspects, the composition further includes tissue filler, non PVF-derived cells, tissue or tissue fragment, demineralized bone, growth factor, biologically inert compound, scaffold, matrix, pharmaceutical agent, polynucleotide encoding a therapeutic agent or a combination thereof. In other aspects, the PVF includes genetically modified cells.

In another embodiment, the invention provides a cell bank of pericytes and/or perivascular cells (PVCs) derived by a method including sonicating a cellular non-structural tissue; collecting a pericyte vascular fraction (PVF); and isolating the pericytes and/or the PVCs from the PVF, wherein the sonication is indirect sonication.

In certain aspects, one or more of the cells expresses at least one of the molecular markers selected from the group consisting of CD3, CD4, CD13, CD14, CD15, CD16, CD19, CD20, CD29, CD31, CD33, CD34, CD36, CD38, CD44, CD45, CD49d, CD54, CD56, CD58, CD61, CD62e, CD62p, CD69, CD71, CD73, CD90, CD104, CD105, CD106, CD117, CD135, CD144, CD146, CD151, CD166, SH3, Thy-1 and a combination thereof. In other aspects, one or more of the cells does not express at least one of the molecular markers selected from the group consisting of CD3, CD4, CD14, CD15, CD16, CD19, CD33, CD38, CD56, CD61, CD62e, CD62p, CD69, CD104, CD135, CD144 and a combination thereof. In various aspects, the pericytes and/or PVCs are genetically modified.

In an additional embodiment, the invention provides a method of isolating a pericyte vascular fraction (PVF) from a cellular non-structural tissue including sonicating the cellular non-structural tissue with an ultrasonic cavitation head; and collecting the PVF, wherein the sonication is indirect sonication.

In certain aspects, the PVF includes perivascular cells (PVCs). In other aspects, the PVCs include pericytes. In various aspects, the distance between the tissue and the ultrasonic cavitation head during sonication is about 0.1-20 millimeters. In one aspect, the distance between the tissue and the ultrasonic cavitation head is about 3-4 millimeters. In various aspects, the tissue is sonicated from about 1 minute to about 9 hours. In one aspect, the tissue is sonicated for about 5-15 minutes. In many aspects, the sonication is performed at about 15-50 kHz. In one aspect, the sonication is performed at about 20 kHz. In certain aspects, the cellular non-structural tissue is human. In some aspects, the cellular non-structural tissue is obtained by surgical excision or aspiration.

In certain aspects, the PVF includes pericytes and may additionally include PVCs. In other aspects, the PVF further includes hematopoietic cells, platelets, Kupffer cells, osteoclasts, megakaryocytes, granulocytes, natural killer (NK) cells, precursor or progenitor cells, CD34+ cells, monocytes, leukocytes, lymphocytes, B cells, T cells, macrophages, neutrophils, neutrophil leukocytes, neutrophil granulocytes or any combination thereof. In one aspect, the cells of the PVF express at least one of the molecular markers selected from the group consisting of CD3, CD4, CD13, CD14, CD15, CD16, CD19, CD20, CD29, CD31, CD33, CD34, CD36, CD38, CD44, CD45, CD49d, CD54, CD56, CD58, CD61, CD62e, CD62p, CD69, CD71, CD73, CD90, CD104, CD105, CD106, CD117, CD135, CD144, CD146, CD151, CD166, SH3, Thy-1 and a combination thereof. In another aspect, the cells of the PVF do not express at least one of the molecular markers selected from the group consisting of CD3, CD4, CD14, CD15, CD16, CD19, CD33, CD38, CD56, CD61, CD62e, CD62p, CD69, CD104, CD135, CD144 and a combination thereof. In an additional aspect, the cells of the PVF are differentiated.

In a further embodiment, the invention provides a method of treating a disease or a disorder in a subject with a pericyte vascular fraction (PVF) including sonicating a cellular non-structural tissue; isolating the PVF; and administering the PVF to the subject, wherein the sonication is indirect sonication.

In various aspects, the PVF further includes a pharmaceutically acceptable carrier, diluent and/or excipient. In certain aspects, the PVF further includes tissue filler, non PVF-derived cells, tissue or tissue fragment, demineralized bone, growth factor, biologically inert compound, scaffold, matrix, pharmaceutical agent, polynucleotide encoding a therapeutic agent or a combination thereof. In other aspects the PVF includes genetically modified perivascular cells and/or pericytes.

In various aspects, the disease or disorder is selected from the group consisting of stroke, diabetes, arthritis, multiple sclerosis and chemotherapy-induced peripheral neuropathy.

In many aspects, the cellular non-structural tissue is autologous or allogenic tissue. In various aspects, the subject is human. In various aspects, the cellular non-structural tissue is obtained by surgical excision or aspiration.

In one aspect, the administration is local or systemic. In some aspects, the PVF is administered by infusion, implantation or injection. In another aspect, the method further includes administering tissue filler, non PVF-derived cells, tissue or tissue fragment, demineralized bone, growth factor, biologically inert compound, scaffold, matrix, pharmaceutical agent, polynucleotide encoding a therapeutic agent or a combination thereof. In some aspects, the tissue filler, the non PVF-derived cells, tissue or tissue fragment, demineralized bone, growth factor, biologically inert compound, scaffold, matrix, pharmaceutical agent, polynucleotide encoding a therapeutic agent or combination thereof is administered prior to, simultaneously with, or after the administration of the PVF.

In other aspects, the method further includes concentrating the isolated PVF. In various aspects, the PVF includes about 10-100 million perivascular cells and/or pericytes. In one aspect, the PVF includes about 50-100 million perivascular cells and/or pericytes. In many aspects, the perivascular cells and/or pericytes concentration in the PVF is about 1-5 million cells per milliliter.

In an additional embodiment, the invention provides a method for improving a tissue in a subject including administering to the tissue a pericyte vascular fraction (PVF), wherein the PVF is derived by a method including sonicating a cellular non-structural tissue, wherein the sonication is indirect sonication. In one aspect, the PVF further includes a pharmaceutically acceptable carrier, diluent and/or excipient.

In many aspects, improving the tissue includes reconstructing, regenerating, augmenting the volume of, and healing the tissue, or any combination thereof. In various aspects, the tissue is skin, facial tissue, buttock, muscle, oral tissue, breast, musculoskeletal tissue, neurological tissue, or cellular tissue; and the facial tissue is a lip and the oral tissue is a gum. In certain aspects, the tissue includes a wrinkle, a wound or a scar. In some aspects, the tissue is allogenic. In other aspects, the method further includes administering tissue filler, non PVF-derived cells, tissue, tissue fragment, demineralized bone, growth factor, drug, biologically active compound, biologically inert compound, scaffold, matrix, pharmaceutical agent, polynucleotide encoding a therapeutic agent or a combination thereof.

In another embodiment, the invention provides a method of processing a cellular non-structural tissue including sonicating the tissue, wherein the sonication is indirect sonication.

In one aspects, intact cells are isolated following the sonication. In many aspects, the cellular non-structural tissue is cadaver tissue. In various aspects, the tissue is stored for 0 to 96 hours prior to processing. In other aspects, the tissue is stored at about 0-7° C. In one aspect, the tissue is stored at 3° C.

In one aspect, the distance between the tissue and an ultrasonic cavitation head is about 3-4 millimeters. In another aspect, the sonication is performed at about 15-50 kHz. In one aspect, the sonication is performed at about 20 kHz. In yet another aspect, the tissue is sonicated for about 5-15 minutes. In various aspects, the tissue is maintained in a container surrounded by water. In one aspect, the water is maintained at the same level as the tissue. In certain aspects, the water temperature is about 0-40° C. In other aspects, the water temperature is about 20° C.

In many aspects, the container further includes a physiologically compatible solution.

In an additional embodiment, the invention provides an apparatus for processing a cellular non-structural tissue including a first container including an ultrasonic cavitation head, a second container, and a weighted cap adhering to the second container.

In one aspect, the second container includes cellular non-structural tissue. In another aspect, the first container additionally includes water, and the water is at the same level as the tissue in the second container. In yet another aspect, the water in the first container is circulating. In an additional aspect, the water temperature is about 20° C.

In various aspects, the frequency of ultrasounds generated by the cavitation head is about 15-50 kHz. In many aspects, the frequency of ultrasounds generated by the cavitation head is about 20 kHz. In one aspect, the distance between the second container and the ultrasonic cavitation head is about 3-4 millimeters.

DETAILED DESCRIPTION OF THE INVENTION

Figure 1:
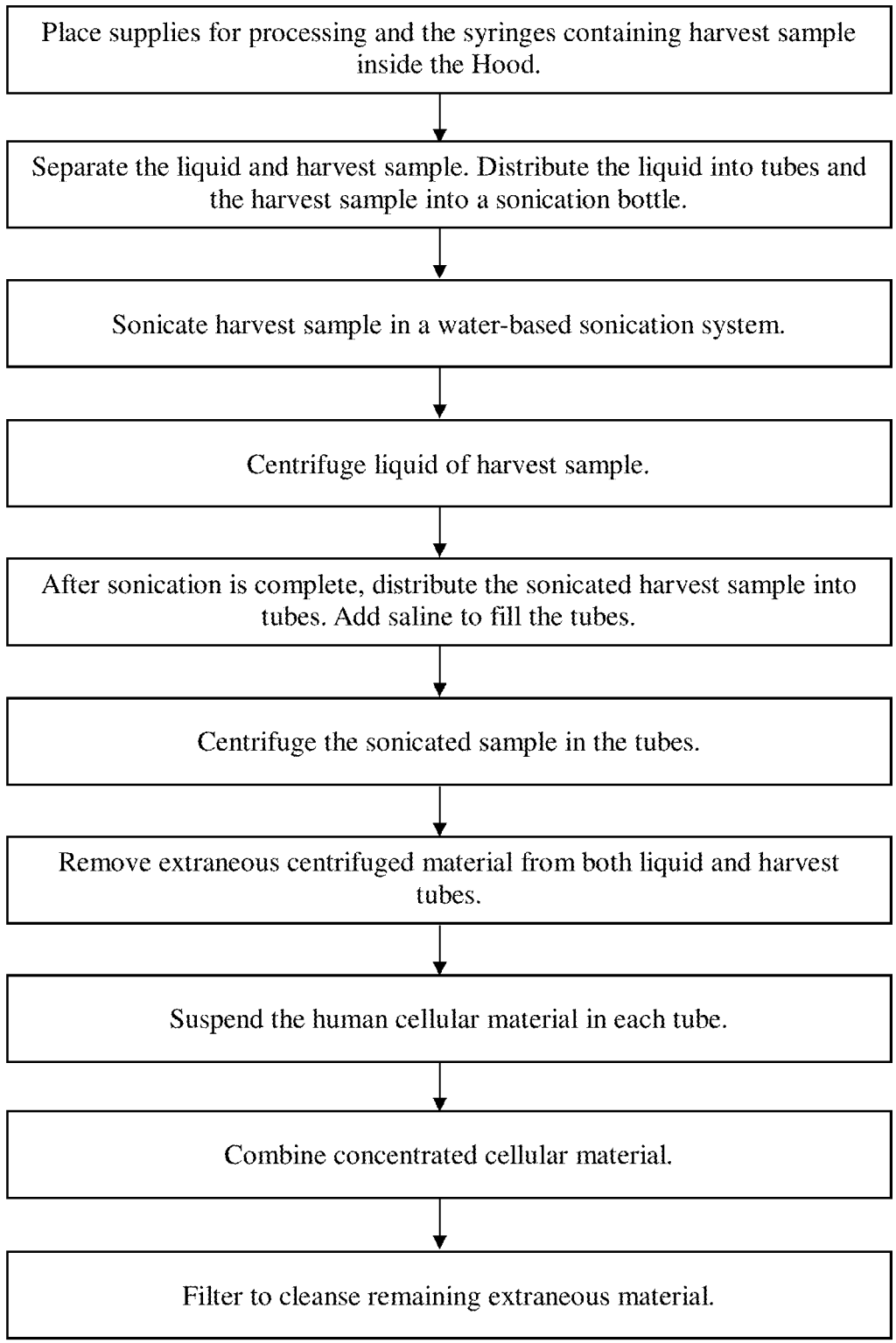
FIG. 1 is a flow chart illustrating the procedure steps followed for the isolation of perivascular cells from a cellular non-structural tissue.

The present invention is based on the seminal discovery that perivascular cells (PVCs) can be isolated from perivascular fraction (PVF) obtained from cellular non-structural tissue by indirect sonication. Also provided are methods of treating cellular non-structural tissue using indirect ultrasonic cavitation to dissociate the pericytes and cells contained within cellular non-structural tissue and thereby obtaining pericyte or perivascular fractions for use in human subjects. These methods preferably do not include the use of any exogenous dissociating enzymes such as collagenase and result in increased numbers of PVCs (about 10-fold greater) than methods which use collagenase.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "about" will be understood by persons of ordinary skill in the art and will vary to some extent based on the context in which it is used.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

In one embodiment, the present invention provides a pericyte vascular fraction (PVF) composition including a PVF derived by a method including sonication of a cellular non-structural tissue; and a pharmaceutically acceptable carrier, diluent and/or excipient, wherein the sonication is indirect sonication.

As used herein, "perivascular fraction" or "PVF", refers to a mixture of stem cells/mesenchymal stem cells, endothelial/progenitors, pericytes, fibroblasts and other cells, generally referred as to by "perivascular cells", "pericytes vascular cells", "Pericytes" or "PVCs", or "capillary perivascular cells" or "CPVCs", obtained from the processing of a cellular non-structural tissue. As used herein, "perivascular cell" refers to pericyte cells found in cellular non-structural tissue, e.g., CD34 expressing hematopoietic cells. The term PVC is also meant to include cells that originate from fluid found in cellular non-structural tissue which can serve as cell-like precursors to a variety of different cell types such as but not limited to pericytes, osteocytes, chondrocytes, muscle and neuronal/glial cell lineages. PVCs make up a subset population derived from cellular non-structural tissue which can be separated from other components of the cellular non-structural tissue using standard culturing procedures or other methods disclosed herein. In addition, perivascular cells can be isolated from a mixture of cells using the cell surface markers disclosed herein. By way of example PVCs may include hematopoietic cells, hematopoietic cells, platelets, Kupffer cells, osteoclasts, megakaryocytes, granulocytes, NK cells, precursor or progenitor cells, CD34+ cells or pericyte cells, (typically found in umbilical cord), CD29+ cells, CD166+ cells, Thy-1+ or CD90+ cells, CD44+ cells, immune cells such as monocytes, leukocytes, lymphocytes, B and T cells, NK cells, macrophages, neutrophil leukocytes, neutrophils, neutrophil granulocytes, and the like including immune and other cells that express one or more of the following markers: CD3, CD14 (macrophage marker), CD19, CD20 (B cell marker), CD29 (integrin unit), CD31 (endothelial, platelet, macrophage, Kupffer cell, dendritic cell, granulocyte, T/NK cells, lymphocytes, megakaryocytes, osteoclasts, neutrophils), CD44 (Hyaluronic acid receptor), CD45 (B and T cell marker), C56, CD73 (lymphocyte differentiation marker), CD105, etc. The PVC also includes cells expressing any of the markers or any combination thereof disclosed in this application.

PVF contains a small percentage of stem cells. Stem cells are undifferentiated cells that have the ability to self-renew indefinitely and to maintain the undifferentiated state. As opposed to embryonic stem cells which can only be isolated from the inner mass of a blastocyst, there are three known accessible sources of adult stem cells: the bone marrow which requires the drilling of a bone, the adipose tissue which is accessible by liposuction, and the blood, from which the cells can be extracted among other cells. Pluripotent stem cells are capable of generating all the cell types of an organism, i.e. cells derived from any of the three germ layers. On the other hand, multipotent stem cells can differentiate into several cell type, but only those of a closely related family of cells, generally the cell types of the organ from which they originate. Most adult stem cells are multipotent but small amounts of pluripotent adult stem cells can be retrieved from umbilical cord or other tissues. Collecting stem cells from a PVF (i.e. adipose tissue) is a less invasive and more efficient process.

As used herein, a "cellular non-structural tissue" refers to tissues that serve predominantly metabolic or other biochemical roles in the body such as hematopoietic, immune, and endocrine functions. Cellular non-structural tissue contain or consist of cells or tissues that are intended for implantation, transplantation, infusion, or transfer into a recipient, but do not physically support or serve as a barrier or conduit, or connect, cover, or cushion, as opposed to structural tissues. Examples of cells or non-structural tissues include reproductive cells or tissues (e.g., oocytes); hematopoietic stem/progenitor cells (e.g., cord blood); lymph nodes and thymus; bone marrow (as a source of hematopoietic stem/progenitor cells); parathyroid glands; peripheral nerve; and pancreatic tissue. As used herein, a "cellular non-structural tissue also refers to the subcutaneous fluid present surrounding and within a tissue, such as adipose tissue, including cells such as pericytes and PVCs. A convenient source of cellular non-structural tissue is that derived from harvest surgery or other surgery, such as liposuction or lipoaspiration; bone marrow aspiration can also be a source of cellular non-structural tissue. However, the source of cellular non-structural tissue or the method of isolation of cellular non-structural tissue is not critical to the invention. During liposuction, for adipose tissue removal, 4 mm cannulas are usually used. For non-structural tissue harvest, as used herein, 2.1 mm cannulas are used, as they allow for a more targeted collection of fluid rather than structural element such as adipose tissue, and for a reduced amount of red blood cells (non-nucleated cells) harvested.

The term "cellular non-structural tissue-derived cell" refers to a cell that originates from cellular non-structural tissue, preferably pericytes are contained therein. The initial cell population isolated from cellular non-structural tissue is a heterogeneous cell population including, but not limited to pericytes, also referred to as PVF or PVCs.

As used herein, "sonicating", "sonication", "ultrasonic cavitation" and the like are used interchangeably without any meaning difference, and refer to the mechanical technique used to separate the PVF from the cellular non-structural tissue. "Ultrasonic cavitation head" refers to the portion of the sonicator that creates the sonication waves that enter in contact with the tissue to dissociate it.

By "pharmaceutically acceptable" it is meant the carrier, diluent or excipient must be compatible with the other ingredients of the formulation and not deleterious to the recipient thereof. For example, the carrier, diluent, or excipient or composition thereof may not cause any undesirable biological effects or interacting in an undesirable manner with any of the other components of the pharmaceutical composition in which it is contained.

In certain aspects, the composition further includes tissue filler, non PVF-derived cells, tissue or tissue fragment, demineralized bone, growth factor, biologically inert compound, scaffold, matrix, pharmaceutical agent, polynucleotide encoding a therapeutic agent or a combination thereof.

As used herein "tissue filler" or "filler" refers to injectable material usually injected into a tissue to restore, ameliorate or improve its appearance. Fillers aim at enhancing or smoothing a tissue, by filling in areas where fat pads have separated. Most fillers are derived from hyaluronic acid or collagen. Other fillers are synthetically derived. Examples of tissue fillers that can be part of the PVF composition of the present invention includes JUVEDERM®, RESTYLANE®, HYLAFORM®, ESTHELIS®, CAPTIQUE®, BELOTERO®, AUTOLOGEN®, COSMODERM®, EVOLENCE®, ZYDERM®, BELLAFILL®, RADIES SE® AND SCULPTRA®.

As used herein, the term "non PVF-derived cells" refers to cells that are part of the PVF but not part of the PVC.

The PVF composition may be used alone or further included a tissue or tissue fragment, referring to a cellular non-structural tissue or fragment thereof, as used for the derivation of the PVF.

The term "growth factor" refers to any naturally occurring substance capable of stimulating cellular growth, proliferation or differentiation. Examples of growth factors that can be part of the PVF composition of the present invention include adrenomedullin (AM), angiopoietin (Ang), autocrine motility factor, bone morphogenetic proteins (BMPs), ciliary neurotrophic factor factor (CNTF), leukemia inhibitory factor (LIF), colony-stimulating factors Macrophage colony-stimulating factor (m-CSF), granulocyte colony-stimulating factor (G-CSF), granulocyte macrophage colony-stimulating factor (GM-CSF), epidermal growth factor (EGF), ephrins (A1, A2, A3, A4, A5, B1, B2, B3, erythropoietin (EPO), fibroblast growth factor (FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, and FGF23), foetal bovine somatotrophin (FBS), glial cell line-derived neurotrophic factor (GDNF), neurturin, persephin, artemin, growth differentiation factor-9 (GDF9), hepatocyte growth factor (HGF), hepatoma-derived growth factor (HDGF), insulin, insulin-like growth factors (IGF-1, and IGF-2), interleukins (IL-1, IL-2, IL-3, IL-4, IL-5, IL-6 and IL-7), keratinocyte growth factor (KGF), migration-stimulating factor (MSF), macrophage-stimulating protein (MSP, also known as hepatocyte growth factor-like protein HGFLP), myostatin (GDF-8), neuregulin (NRG1, NRG2, NRG3, NRG4), brain-derived neurotrophic factor (BDNF), nerve growth factor (NGF), neurotrophin (NT-3, NT-4), placental growth factor (PGF), platelet-derived growth factor (PDGF), eenalase (RNLS), T-cell growth factor (TCGF), thrombopoietin (TPO), transforming growth factor (TGF-$\alpha$, TGF-$\beta$), tumor necrosis factor-alpha (TNF-$\alpha$), vascular endothelial growth factor (VEGF) and Wnt proteins.

"A biologically inert compound" refers to any compound that would not elicit any biological activity.

As used herein "pharmaceutical agent" refers to any molecule, compound or chemical substance that is usually used to treat, cure, prevent or diagnose a disease or condition. The terms can be interchangeably used along with "drug", or "biologically active compound". Examples of drugs that can be part of the PVF composition of the present invention include any pharmaceutical agent known in the art to treat a disease or condition.

As used herein, the term "polynucleotide" refers to nucleic acid such as deoxyribonucleic acid (DNA) or ribonucleic acid (RNA). Nucleic acids include but are not limited to genomic DNA, cDNA, mRNA, iRNA, miRNA, tRNA, ncRNA, rRNA, and recombinantly produced and chemically synthesized molecules such as aptamers, plasmids, anti-sense DNA strands, shRNA, ribozymes, nucleic acids conjugated and oligonucleotides. According to the invention, a nucleic acid may be present as a single-stranded or double-stranded and linear or covalently circularly closed molecule. A nucleic acid can be isolated. The term "isolated nucleic acid" means, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "polynucleotide encoding a therapeutic agent" as used herein refers nucleic acids sequences that have the ability to act on their own as a therapeutic agent, or that encode a peptide, polypeptide or protein that is a therapeutic agent. It includes "antisense nucleic acids", "aptatmers" and "peptide/polypeptide/protein encoding nucleic acids". Anti sense nucleic acids are oligomers of about 50 monomer units or fewer, which have the ability to hybridize in a sequence-specific manner to a targeted single-stranded RNA or DNA molecule. Members of this class include ordinary DNA and RNA oligomers, DNA and RNA having modified backbones, including but not limited to phosphorothioates, phosphorodithioates, methylphosphonates, and peptide nucleic acids, 2'-deoxy derivatives, and nucleic acid oligomers that feature chemically modified purine and pyrimidine bases, or have been lipophilically modified and/or PEGylated to modify their pharmacodynamics. Oligomers that serve as precursors for such agents, such as hairpin RNAs that are converted to siRNAs within cells, are also considered to be within this class. Nucleic acid-based therapeutic agents such as aptamers are oligomers of about 50 monomer units or fewer, which have the ability to bind with structural specificity to a non-oligonucleotide target molecule, or to an oligonucleotide in a manner other than through sequence-specific hybridization. Members of this class include DNA and RNA aptamers, and modifications thereof including but not limited to mirror-image DNA and RNA ("Spiegelmers"), peptide nucleic acids, and nucleic acid oligomers that have otherwise been chemically modified as described above. Again, any of these species may also feature chemically modified purines and pyrimidines or may be lipophilically modified and/or PEGylated (see M. Rimmele, Chembiochem. 4: 963-71 (2003); and A. Vater and S. Klussmann, Curr. Opin. Drug Discov. Devel. 6: 253-61 (2003), for recent reviews of aptamer technology). It will be appreciated that many members of this second class will, in addition to their structure-specific affinity for the target molecule, have sequence-specific affinity for a putative DNA or RNA sequence. Peptide/polypeptide/protein encoding nucleic acids are sequence that are transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

The term "vector", "expression vector", or "plasmid DNA" is used herein to refer to a recombinant nucleic acid construct that is manipulated by human intervention, and that contains two or more nucleotide sequences that are linked in a manner such that the product is not found in a cell in nature. In particular, the two or more nucleotide sequences can be operatively linked, such as a gene encoding a protein of interest, one or more protein tags, functional domains and the like. For example, expression vector usually comprises one or more promoters, operably linked to the nucleic acid of interest. As used herein, a promoter is intended mean a polynucleotide sequence capable of facilitating transcription of genes in operable linkage with the promoter. Additional regulatory elements that may be useful in vectors, include, but are not limited to, polyadenylation sequences, translation control sequences (e.g., an internal ribosome entry segment, IRES), enhancers, or introns.

In other aspects, the PVF includes genetically modified cells. As used herein, the phrase "genetically modified" is the direct manipulation of an organism's genes using biotechnology. Genetic modification includes the transfer of genes and/or the insertion or deletion of nucleic acids into or from a cell. For example, the cells of the PVF composition may be genetically modified to contain an additional polynucleotide that encodes for a therapeutic agent or for an inhibiting nucleic acid, to remove a gene of interest, or to modulate the expression of a gene of interest. Examples of nuclear acids include, a ribozyme, an antisense oligonucleotide, a double stranded RNA, a double-stranded interfering RNA (iRNA), a triplex RNA, an RNA aptamer, and at least a portion of an antibody molecule that binds to the gene product and inhibits its activity. Methods for genetically modifying a cell are well known in the art.

For example, the cell population may be modified by insertion of DNA. Gene transfer techniques could be by any technology known in the art including but not limited to adenoviral transduction, "gene guns", liposome-mediated transduction, and retrovirus or lentivirus-mediated transduction. Non-viral based techniques may also be performed. In an alternative embodiment, the cells can be placed in cell culture in such a way as to change, enhance, or supplement the function of the cells for derivation of a cosmetic, structural, or therapeutic purpose.

As a non-limiting example, cells may, for example, be genetically modified to express a gene encoding a pro-osteogenic growth factor which allows the cells to act as their own source of growth factor during bone healing or fusion.

In another embodiment, the invention provides a cell bank of pericytes and/or perivascular cells (PVCs) derived by a method including sonicating a cellular non-structural tissue; collecting a pericyte vascular fraction (PVF); and isolating the pericytes and/or the PVCs from the PVF, wherein the sonication is indirect sonication.

The term "cell bank" refers to the storage of several PVCs collected from various PVFs isolated from different subjects. The cell bank may contain cells with specific properties, such as cells which express or do not express specific cell surface markers. The cell bank may contain cells which have been separated by cellular characteristics, such as cell surfaces markers.

After collecting a PVF or PVC a portion of the cell population may be stored for later implantation/infusion. The population may be divided into more than one aliquots or units such that part of the population of cells and/or precursor cells is retained for later application while part is applied immediately to the patient. Moderate to long-term storage of all or part of the cells in a cell bank is also within the scope of this invention. In such an embodiment, the cells may be mixed with one or more units of fresh or preserved cellular non-structural tissue to provide a composition containing the cells at a higher concentration than a unit of cellular non-structural tissue prior to processing.

The optimal freezing and storage condition of the PVF of the invention is achieved without the use of culture media, but following industry standards using Dextran which is a low molecular weight dextrose product. When used in correct proportions dextrose eliminates the expansion and explosion of stored cells during freezing. Regular DMSO can be used as well. The cells can be frozen in cryovials, or any container appropriate for freezing. Freezing conditions includes a −80° C. freezer or a liquid nitrogen container.

Thawing process can be necessary for quality control check, or for subsequent use of the cells. In both cases, frozen vials are removed from freezer (or liquid nitrogen container) and immediately dipped in a water bath preheated at 37° C.

In certain aspects, one or more of the cells expresses at least one of the molecular markers selected from the group consisting of CD3, CD4, CD13, CD14, CD15, CD16, CD19, CD20, CD29, CD31, CD33, CD34, CD36, CD38, CD44, CD45, CD49d, CD54, CD56, CD58, CD61, CD62e, CD62p, CD69, CD71, CD73, CD90, CD104, CD105, CD106, CD117, CD135, CD144, CD146, CD151, CD166, SH3, Thy-1 and a combination thereof. In other aspects, one or more of the cells does not express at least one of the molecular markers selected from the group consisting of CD3, CD4, CD14, CD15, CD16, CD19, CD33, CD38, CD56, CD61, CD62e, CD62p, CD69, CD104, CD135, CD144 and a combination thereof.

For example the PVCs of the PVF includes cells that express at least one protein selected from the group consisting of CD13, CD14, CD29, CD31, CD34, CD36, CD44, CD45. CD49d, CD54, CD58, CD71, CD73, CD90, CD105, CD106, CD151 and SH3, or CD13, CD29, CD34, CD36, CD44, CD49d, CD54, CD58, CD71, CD73, CD90, CD105, CD106, CD151 and SH3 and/or CD31, CD45, CD117 and CD146 and do not express CD56.

In other examples, the PVCs includes cells that express at least one protein selected from the group consisting of CD3, CD4, CD14, CD15, CD16, CD19, CD33, CD38, CD56, CD61, CD62e, CD62p, CD69, CD104, CD and CD144, and do not express CD3, CD4, CD14, CD15, CD16, CD19, CD33, CD38, CD56, CD61, CD62e, CD62p, CD69, CD104, CD135 and CD144 or express CD49d and do not express CD56.

The phrase "molecular marker" is used alternatively with the phrases "cellular marker", "cell surface marker" or "cell surface protein" and refers to any protein that is expressed at the surface of a cell, and that can be used to differentiate cell types.

"Polypeptide" or "protein" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides, typically over 100 amino acids. The term "peptide" typically refers to short polypeptides, typically under 100 amino acids.

By way of example, it is provided that CD3 and CD14 are macrophage markers; CD19 and CD20 are B cell markers; CD29 is an integrin unit; CD31 is expressed by endothelial, platelet, macrophage, Kupffer cell, dendritic cell, granulocyte, T/NK cells, lymphocytes, megakaryocytes, osteoclasts and neutrophils; CD44 is a hyaluronic acid receptor; CD45 is a B and T cell marker; C56 and CD73 are lymphocyte differentiation markers. Cells expressing any of the markers or any combination thereof are also disclosed in this application.

In various aspects, the pericytes and/or PVCs are genetically modified.

In another preferred embodiment the invention provides PVCs derived from cellular non-structural tissue that do not include any exogenous collagenase. As used herein "endogenous" refers to any material from or produced inside an organism, cell or system. "Exogenous" refers to any material introduced from or produced outside an organism, cell, or system. In particular exogenous may refer to a material that is not present in the treated cellular non-structural tissue.

In an additional embodiment, the invention provides a method of isolating a pericyte vascular fraction (PVF) from a cellular non-structural tissue including sonicating the cellular non-structural tissue with an ultrasonic cavitation head; and collecting the PVF, wherein the sonication is indirect sonication.

The invention provides a novel method of obtaining a pericyte or pericyte vascular fraction from cellular non-structural tissue that does not include the use of collagenase or other enzymes to digest the collagen bonds that hold together the tissue. While collagenase works well for this purpose, and indeed is conventionally used by those skilled in the art to degrade collagen and separate the tissue into discrete cells, the use of this enzyme may be disadvantageous for cellular products that are to be used in humans, e.g., cells or cell fractions which are to be used in tissue reconstruction or regeneration, e.g., breast reconstruction procedures, cosmetic skin rejuvenation or usage in cosmetic tissue fillers that are used during plastic surgery. Particularly the FDA may consider that the use of this enzyme (to derive desired cells) results in a "maximally manipulated" cellular product. This is disadvantageous as the use of collagenase would potentially place pericyte or pericyte vascular cells derived from cellular non-structural tissue in a category that requires drug approval, even if the cell fraction is to be used cosmetically and not clinically.

Also, the use of enzymes such as collagenase is further disfavored as these enzymes result in more cell death, thereby reducing the number of the desired cells which are isolatable, and further this results in more cellular debris, thereby resulting in a less useful cell product, especially if the cells are to be used therapeutically. Accordingly it would be desirable to provide alternative methods, e.g., mechanical methods, that produce a pericyte or pericyte vascular fraction (containing pericyte or pericyte cells, cells, and other cells found in cellular non-structural tissues) which is suitable for administration to patients via local or systemic administration such as via injection, infusion, implantation, topical administration, or which is administered in association with implants, matrices, tissue fillers, wherein the cellular non-structural tissue derived composition does not include collagenase and is not "maximally manipulated" according to the FDA.

The present invention discloses that cellular non-structural tissues, e.g., derived from surgical excision or aspirated via harvest may be treated ex vivo by ultrasonic cavitation for a sufficient amount of time to concentrate and cleanse the pericytes and the cells contained therein thereby releasing the pericyte vascular fraction cells contained within the outer layer of blood vessel walls contained in the cellular non-structural tissue including pericyte and pericyte cells, precursor cells, and other cell types which constitute the "pericyte vascular fraction" or the "pericyte vascular fraction". The treatment of cellular non-structural tissue by ultrasonic cavitation under appropriate conditions such as exemplified in the examples, not only concentrates and cleanses the pericytes, but further concentrates and cleanses the cells contained therein, without adversely affecting the viability of pericyte and pericyte cells, thereby releasing high numbers of viable pericyte and pericyte cells, precursor cells, and other cell types which constitute the "pericyte vascular fraction" or the "pericyte vascular fraction" which pericyte and pericyte cells may be recovered and used in desired cosmetic or therapeutic methods wherein these cells are of beneficial value.

This mechanical means is achieved in the absence of protease in order to derive a pericyte or pericyte vascular fraction from cellular non-structural tissue suitable for administration to human subjects has not previously been successfully used when the present invention was disclosed, morevover, the present invention reproducibly results in very high numbers of viable pericyte vascular fraction cells, which are well suited for use in cell therapy or cosmetic procedures.

In the present invention ultrasonic cavitation is used to mechanically treat cellular non-structural tissue ex vivo in the absence of collagenase to concentrate and cleanse pericytes and the blood cells contained therein and the resultant sonically treated composition (from which the pericytesis removed) is then used to obtain a pericyte or pericyte vascular fraction which can be infused directly in patients in need thereof or it can be further processed to purify (and expand in culture if desired) desired cell types such as pericyte or pericyte cells, cells, and other cells found in cellular non-structural tissue. These fractions and cells may be used in patients such as for acute and chronic inflammatory conditions but not limited to degenerative diseases, endocrinological conditions, tissue reconstruction, tissue regeneration, wound healing, augmentation or reconstruction, treatment of orthopedic problems, treatment of arthritis, treatment of migraine, treatment of multiple sclerosis, treatment of autism, treatment of diabetes, treatment of wounds, treatment of ulcers, treatment of COPD. In certain embodiments the cells are used for the treatment of stroke, diabetes, arthritis, multiple sclerosis and chemotherapy-induced peripheral neuropathy.

The present invention produces pericytes or pericyte vascular fractions from perivascular tissues contained in cellular non-structural tissue which contains perivascular cells and other cells found in the non-structural tissue without the use of collagenase or another enzyme that cleaves collagen bonds. Specifically, the invention produces a pericyte or pericyte vascular fraction from cellular non-structural tissue, which method includes treating cellular non-structural tissue with ultrasonic cavitation under conditions whereby that the pericytes in the sample are concentrate and cleanse, and in addition under ultrasonication conditions whereby the cells found in the pericytes are further concentrate and cleansed without adversely affecting the viability of pericyte and pericyte cells contained therein. The judicious optimization of ultrasonication conditions as described herein, allows ultrasonication methods to be used in the absence of protease treatment to release the desired pericyte or pericyte vascular cells from the cells found in the cellular non-structural tissue without adversely affecting the pericyte and pericyte cells with substantial lysis or degradation of the pericyte and pericyte cells. Preferably, the methods will not include the addition of an enzyme that breaks down collagen such as a collagenase or other endopeptidase. The pericyte or pericyte vascular fraction and specific cell types contained therein are isolated from cellular non-structural tissue surgically obtained from the pericyte or pericyte compartment of the body of a allogenic or autologous donor or derived from a harvest derived aspirate.

As used herein, the term "allogeneic" is meant to refer to any material derived from a different donor than the same individual harvested. As used herein, the term "autologous" is meant to refer to any material derived from the same individual to which it is later to be re-introduced.

The method and device disclosed herein include the use of indirect ultrasonic cavitation of the cellular non-structural tissue containing the perivascular fractions (PVF) containing targeted cells placed into a sterile container which is of material which allows proper transfer of created cavitation waves from the sonication head through the container into the perivascular fractions (PVF) without direct violation of cells currently or previously use to explode or lyse structural tissue containing stromal vascular fractions.

The present invention relies on the ex vivo processing of a cellular non-structural tissue, in the absence of collagenase, by ultrasonic cavitation for a sufficient amount of time to concentrate and cleanse the pericytes and the cells contained within the outer layer of blood vessel walls contained in the cellular non-structural tissue. The present invention reproducibly results in very high numbers of viable pericyte vascular fraction cells, which are well suited for use in cell therapy or cosmetic procedures.

In certain aspects, the PVF includes perivascular cells (PVCs). In other aspects, the PVCs include pericytes.

In various aspects, the distance between the tissue and the ultrasonic cavitation head during sonication is about 0.1-20 millimeters. In one aspect, the distance between the tissue and the ultrasonic cavitation head is about 3-4 millimeters.

As used herein, when the distance between the tissue and the ultrasonic cavitation head is about 0 millimeter and/or in direct contact, the method is a direct ultrasonic cavitation. In preferred conditions, the ultrasonic cavitation is indirect, and there is a minimal distance between the tissue and the ultrasonic cavitation head. During indirect sonication the ultrasonic cavitation occurs through a barrier which blocks the harvested tissues from contacting the ultrasonic cavitation device. During direct sonication a sterility concerns increase, and the treatment of all tissues evenly and obtaining of consistent repetitive results could also be compromised.

In another embodiment the method and device will include the use of indirect ultrasonic cavitation of the cellular non-structural tissue containing the PVF containing PVCs placed into a sterile container. The container will be made of material which allows proper transfer of created cavitation waves from the sonication head through the container into the tissue without damaging the cells). Any device that can safely process a wide range of organic and inorganic materials—from microliters to liters can be used. Non limiting examples of devices which may be used include Qsonica Q500S, Vibra-Cell™, HIELSCHLER SONIC 200, and SONIC 200.

In various aspects, the tissue is sonicated from about 1 minute to about 9 hours. In one aspect, the tissue is sonicated for about 5-15 minutes. In many aspects, the sonication is performed at about 15-50 kHz. In one aspect, the sonication is performed at about 20 kHz.

In certain aspects, the cellular non-structural tissue is human. Preferably the cellular non-structural tissue is mammalian, most preferably the cellular non-structural tissue is human, however, the tissue may be from any organism having pericyte tissue. The tissue can be obtained from any animal, alive or dead, as long as PVCs within the animal are viable.

As used herein, "adipose tissue", "fat", or "fat tissue" are used interchangeably. In many aspects, the tissue is obtained by surgical excision or aspiration. One source of human cellular non-structural tissue is that derived from harvest surgery or other surgery. However, the source of cellular non-structural tissue or the method of isolation of cellular non-structural tissue is not critical to the invention. Non-structural or cellular tissues can as a way of example be collected from subcutaneous areas around the abdomen, thighs and low back, i.e., inguinal, retroperitoneal and gonadal, or any combination thereof. Typically, human cellular non-structural tissue is obtained from a living donor using surgical excision or suction.

After ultrasonic cavitation the pericytes (at the top of the composition) can be removed and the remaining fraction further concentrated or assayed (such as by flow cytometry) for the presence of desired cell types including and precursor cells, immune cells, osteoclasts, hematopoietic cells, and other cell types disclosed herein.

Alternatively, after ultrasonic cavitation the pericyte or pericyte cells can be identified from the sample such as by flow cytometry or may be fractionated into different cell types using fluorescence activated call sorting (FACS) based on cell surface antigens which are specific to perivascular cells or other cell lineages contained in cellular non-structural tissue.

In other aspects, the pericytes are isolated by flow cytometry. The PVCs can be identified from a sample by flow cytometry by detecting the molecular markers expressed at the surface of the cells. The cell may also be fractionated into different cell types using fluorescence activated cell sorting (FACS) based on cell surface antigens which are specific to perivascular cells or other cell lineages contained in cellular non-structural tissue.

Cells of the PVF can be characterized by the cellular markers expressed at their surface including: CD3, CD14 (macrophage marker), CD19, CD20 (B cell marker), CD29 (integrin unit) CD31 (endothelial, platelet, macrophage, Kupffer cell, granulocyte, T/NK cells, lymphocytes, megakaryocytes, osteoclasts, neutrophils, et al.), CD44 (Hyaluronic acid receptor) CD45 (B and T cell marker), C56, CD73 (lymphocyte differentiation marker), CD105.

Alternatively, PVCs can be separated immunohistochemically by selecting for specific cell markers using suitable materials and methods, e.g., panning, using magnetic beads, or affinity chromatography. Suitable markers include any of the markers disclosed in this application or any combination thereof. The resultant purified cells may be injected into desired organs to effect tissue repair, e.g. into heart muscle to effect repair of the heart muscle, after a heart attack, into brain or spinal fluid to effect neural or nerve regeneration, such as Parkinson's or Alzheimer's patients, into the bone or cartilage of individuals in need thereof such as individuals suffering from age, exertion, or disease related bone or cartilage loss.

In certain aspects, the PVF includes pericytes and may additionally include PVCs. In other aspects the PVF further includes hematopoietic cells, platelets, Kupffer cells, osteoclasts, megakaryocytes, granulocytes, natural killer (NK) cells, precursor or progenitor cells, CD34+ cells, monocytes, leukocytes, lymphocytes, B cells, T cells, macrophages, neutrophils, neutrophil leukocytes, neutrophil granulocytes or any combination thereof. In one aspect, the cells of the PVF express at least one of the molecular markers selected from the group consisting of CD3, CD4, CD13, CD14, CD15, CD16, CD19, CD20, CD29, CD31, CD33, CD34, CD36, CD38, CD44, CD45, CD49d, CD54, CD56, CD58, CD61, CD62e, CD62p, CD69, CD71, CD73, CD90, CD104, CD105, CD106, CD117, CD135, CD144, CD146, CD151, CD166, SH3, Thy-1 and a combination thereof. In another aspect, the cells of the PVF do not express at least one of the molecular markers selected from the group consisting of CD3, CD4, CD14, CD15, CD16, CD19, CD33, CD38, CD56, CD61, CD62e, CD62p, CD69, CD104, CD135, CD144 and a combination thereof.

As used herein, the term "phenotypic characteristics" should be construed to mean at least one of the following characteristics: morphological appearance, the expression of a specific protein, a staining pattern or the ability to be stained with a substance. PVCs can be characterized based on morphological, biochemical or molecular-based methods. PVCs are small and agranular cells, accordingly, using a flow cytometer PVCs can be characterized based on their size and granularity.

Because PVCs tend to have longer telomeres than differentiated cells, PVCs can be characterized by assaying the length of the telomere or by assaying telomerase activity.

PVCs can also be separated from the other cells of the pellet immunohistochemically by selecting them for specific cellular markers using suitable materials and methods, e.g., panning, using magnetic beads, or affinity chromatography.

In an additional aspect, the cells of the PVF may be differentiated. As previously detailed, PVF includes a mixture of cells, which encompasses differentiated cells, and undifferentiated cells. "Differentiated" a continuum ranging from stem cells to partially differentiated cells to fully differentiated cells.

"Fully differentiated" is used herein to refer to a cell that has achieved a terminal state of maturation such that the cell has developed fully and demonstrates biological specialization and/or adaptation to a specific environment and/or function. Typically, a differentiated cell is characterized by expression of genes that encode differentiation-associated proteins in that cell. A "differentiated perivascular cell" is an perivascular adult cell isolated from any cellular non-structural tissue that has differentiated as defined herein. An "undifferentiated perivascular cell" is a cell isolated from cellular non-structural tissue, but that has no detectably expressed proteins or other phenotypic characteristics indicative of biological specialization and/or adaptation. Depending on the application, undifferentiated cells may be cultured under specific conditions to induce their differentiation into a desired cell type. "Differentiation medium" is used herein to refer to a cell growth medium comprising an additive or a lack of an additive such that a cell, a cellular non-structural tissue derived pericyte cell, an embryonic cell, an ES-like cell, a MSCs, a neurosphere, a NSC or other such progenitor cell, that is not fully differentiated when incubated in the medium, develops into a cell with some or all of the characteristics of a differentiated cell.

Desired cell lineages include for example fibroblasts, neural cells, hematopoietic cells, myocytes, chondrocytes, and other cell types. As used herein, when a cell is said to be "differentiating", the cell is in the process of being differentiated.

The terms "precursor cell," "progenitor cell," and " cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. In contrast to pluripotent cells, lineage-committed progenitor cells are generally considered to be incapable of giving rise to numerous cell types that phenotypically differ from each other. Instead, progenitor cells give rise to one or possibly two lineage-committed cell types. As used herein, the term "multipotential" or "multipotentiality" is meant to refer to the capability of a cell to differentiate into more than one type of cell.

As used herein, the term "late passaged cellular non-structural tissue-derived pericyte cell," refers to a cell exhibiting a less immunogenic characteristic when compared to an earlier passaged cell. The immunogenicity of an cellular non-structural tissue-derived pericyte cell corresponds to the number of passages. Preferably, the cell has been passaged up to at least the second passage, more preferably, the cell has been passaged up to at least the third passage, and most preferably, the cell has been passaged up to at least the fourth passage.

To fulfill certain therapeutic needs, the isolated cells may be cultured under conditions that give rise to desired cell lineages. For example pericyte and PVCs comprised in the fraction can be differentiated into desired cell types including fibroblasts, neural cells, hematopoietic cells, myocytes, chondrocytes, and other cell types. For example, fibroblast populations may be seeded on a scaffold, which may be used in wound healing. An "isolated cell" refers to a cell which has been separated from other components and/or cells which naturally accompany the isolated cell in a tissue or mammal.

Undifferentiated human pericyte cells express a distinct immunophenotype (phenotype of a cell in terms of the surface protein profile of a cell) based on flow cytometry analyses and, following induction, produce additional pericyte specific proteins. Human perivascular adult cells displayed multipotentiality (capability of a cell to differentiate into more than one type of cell), with the capability of differentiating along the pericyte, chondrocyte, myogenic, neuronal, and osteoblast lineages.

In a further embodiment, the invention provides a method of treating a disease or a disorder in a subject with a pericyte vascular fraction (PVF) including sonicating a cellular non-structural tissue; isolating the PVF; and administering the PVF to the subject, wherein the sonication is indirect sonication.

After ultrasonic cavitation, the isolated pericyte or pericyte cells or other cells are derived therefrom can be infused, implanted, injected or administered into a patient for a specific acute inflammatory, chronic inflammatory, endocrinologic, cosmetic or therapeutic procedure.

Alternatively, the isolated pericyte or pericyte cells or other cells are derived therefrom can be used to promote healing of acute and chronic inflammatory conditions but not limited to degenerative diseases, endocrinological conditions, tissue reconstruction, tissue regeneration, wound healing, augmentation or reconstruction, treatment of orthopedic problems, treatment of arthritis, treatment of migraine, treatment of multiple sclerosis, treatment of autism, treatment of diabetes, treatment of wounds, treatment of ulcers, treatment of COPD.

The present invention does not target stem cells but all the cells found in the subcutaneous tissues released by capillaries and arterioles and is cleansing them from any debris remaining from the structural tissue, which provides higher cell counts than any recordings known to date without culturing, growing, or expanding the cells nor using collagenous enzymes. With these higher cell counts, cells can be stored and used to then conduct multiple treatments and injections as deemed necessary. The process is done with indirect sonic cavitation of the cellular tissue harvested to cleanse the cellular tissue of debris from structural tissue. This allows to concentrate, cleanse and store the cells which can then be infused, implanted or injected according to the protocols to treat the disease states targeted.

A "disease" or a "disorder" is an abnormal state of health of a subject that negatively affects the structure and/or function of part of all of an organ or the entire organism of the subject. Disease and disorder are pathologic conditions that are diagnosed based on the symptoms experienced by the subject. Depending on the disease or disorder, treatments and/or prophylactic treatments may exist. As used herein, the term "disease, disorder or condition of the central nervous system" is meant to refer to a disease, disorder or a condition which is caused by a genetic mutation in a gene that is expressed by cells of the central nervous system or cells that affect the central nervous system such that one of the effects of such a mutation is manifested by abnormal structure and/or function of the central nervous system, such as, for example, defective myelin. Such genetic defects may be the result of a mutated, non-functional or under-expressed gene in a cell of the central nervous system.

The term "subject" as used herein refers to any individual or patient to which the subject methods are performed. Generally the subject is human, although as will be appreciated by those in the art, the subject may be an animal. Thus other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject.

The term "treatment" is used interchangeably herein with the term "therapeutic method" and refers to both 1) therapeutic treatments or measures that cure, slow down, lessen symptoms of, and/or halt progression of a diagnosed conditions or disorder, and 2) and prophylactic/preventative measures. Those in need of treatment may include individuals already having a particular medical disorder as well as those who may ultimately acquire the disorder (i.e., those needing preventive measures). To "treat" a disease as the term is used herein, means to reduce the frequency of the disease or disorder, reducing the frequency with which a symptom of the one or more symptoms disease or disorder is experienced by the subject.

A "therapeutic" treatment is a treatment administered to a patient who exhibits signs of pathology for the purpose of diminishing or eliminating those signs and/or decreasing or diminishing the frequency, duration and intensity of the signs. The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome. Such amount should be sufficient to a beneficial effect to the subject to which the compound is administered. The effective amount can be determined as described herein. As used herein, a "therapeutically effective amount" is the amount of cells which is sufficient to provide a beneficial effect to the subject to which the cells are administered.

The terms "administration of" and or "administering" should be understood to mean providing a pharmaceutical composition in a therapeutically effective amount to the subject in need of treatment.

The present invention discloses a method of treating a patient which includes steps of providing a tissue removal system; removing cellular non-structural tissue from a patient using the tissue removal system, the cellular non-structural tissue having a concentration of cells; processing at least a part of the cellular non-structural tissue by use of ultrasonic sonication for a time sufficient to concentrate all or most of the pericytes and release the pericyte and pericyte vascular cells into a suitable fluid medium, e.g. phosphate buffered saline solution, allowing the treated solution to settle such that the pericytes rise to the top of the solution and the pericytes is removed in order to obtain a concentrate and cleansed pericyte or pericyte vascular fraction containing regenerative cells other than the concentration of regenerative cells of the cellular non-structural tissue before processing, wherein the processing occurs within a sterile, closed or functionally closed system; and administering the concentrate and cleansed regenerative cells to a patient, to thereby treat the patient.

The present method requires to provide a tissue removal system, which, in certain embodiments, allows the cells to be administered to the patient without being removed from the system or exposed to the external environment of the system before being administered to the patient. Providing such a closed system reduces the possibility of contamination of the material being administered to the patient. Thus, processing the cellular non-structural tissue in a closed system provides advantages because the active cell population is more likely to be sterile. In such an embodiment, the only time the cells and/or precursor cells are exposed to the external environment, or removed from the system, is when the cells are being withdrawn into an application device and being administered to the patient. In one embodiment, the application device can also be part of the closed system. Thus, the cells used in these embodiments are not processed for culturing, or cryopreserved.

In various aspects, the PVF further includes a pharmaceutically acceptable carrier, diluent and/or excipient.

In certain aspects, the PVF composition further includes tissue filler, non PVF-derived cells, tissue or tissue fragment, demineralized bone, growth factor, biologically inert compound, scaffold, matrix, pharmaceutical agent, polynucleotide encoding a therapeutic agent, or a combination thereof.

Alternatively, the PVF composition can be referred to as a graft. As used herein, a "graft" refers to a cell, tissue or organ that is implanted into an individual, typically to replace, correct or otherwise overcome a defect. A graft may further include a scaffold. The tissue or organ may consist of cells that originate from the same individual; this graft is referred to herein by the following interchangeable terms: "autograft", "autologous transplant", "autologous implant" and "autologous graft". A graft including cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

In other aspects the PVF includes genetically modified perivascular cells and/or pericytes.

In various aspects, the disease or disorder is selected from the group consisting of stroke, diabetes, arthritis, multiple sclerosis and chemotherapy-induced peripheral neuropathy. Generally, the disease or disorder can be selected from the group consisting of orthopedic condition, endocrinological condition, acute or chronic inflammatory condition, rheumatic disorder, wound, degenerative disease, damaged or injured tissue, migraine and autism.

As used herein, "orthopedic condition" refers to any condition that affect the musculoskeletal system, most commonly the bones and joints. The conditions may be genetic, traumatic, age-related or caused by overuse. Examples of orthopedic condition include arthritis (osteoarthritis, rheumatoid arthritis), bursitis, elbow pain and problems (cubital tunnel syndrome, lateral epicondylitis (tennis elbow), medial epicondylitis (golfer's or baseball elbow)), fibromyalgia, chronic pain, foot pain and problems, fractures, hip fracture, low back pain, hand pain and problems (carpal tunnel syndrome), knee pain and problems (ligament injuries to the knee, torn meniscus), kyphosis, neck pain and problems, osteoporosis, Paget's disease of the bone, scoliosis, shoulder pain and problems, slow fracture, non-union fracture, bone or cartilage loss, neck and back pain, osteogenesis imperfect, traumatic musculoskeletal condition, inherited musculoskeletal condition and soft-tissue injuries.

As used herein, "endocrinological condition" refers to any disease or condition that occurs when the endocrine system does not function properly, which is responsible for abnormal hormonal production. Examples of endocrinological condition include acromegaly, Addison's disease, adrenal cancer, adrenal disorders, anaplastic thyroid cancer, Cushing's syndrome, De Quervain's thyroiditis, diabetes, follicular thyroid cancer, gestational diabetes, goiters, Graves' disease, growth disorders, growth hormone deficiency, Hashimoto's thyroiditis, hurthle cell thyroid cancer, hyperglycemia, hyperparathyroidism, hyperthyroidism, hypoglycemia, hypoparathyroidism, hypothyroidism, low testosterone, medullary thyroid cancer, multiple endocrine neoplasia type 1 (MEN 1), MEN 2a, MEN 2b, menopause, metabolic syndrome, obesity, osteoporosis, papillary thyroid cancer, parathyroid diseases, pheochromocytoma, pituitary disorders, pituitary tumors, polycystic ovary syndrome, prediabetes, reproduction, silent thyroiditis, thyroid cancer, thyroid diseases, thyroid nodules, thyroiditis, Turner syndrome, type 1 diabetes, and type 2 diabetes.

Inflammation is a normal, healthy response that occurs after injury or in certain conditions, the term "inflammatory condition" refers to an abnormal inflammation, which results in chronic pain, redness, swelling, stiffness, and damage to normal tissues. Examples of inflammatory condition include Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Anti synthetase syndrome, Arthritis, Asthma; Atherosclerosis Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Diverticulitis, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Gout, Graves' disease, Guillain-Barré syndrome, Hashimoto's encephalopathy, Hashimoto's thyroiditis, Henoch-Schonlein purpura, Hepatitis, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Irritable bowel syndrome, Juvenile idiopathic arthritis aka Juvenile rheumatoid arthritis, Kawasaki's disease, Lambert-Eaton myasthenic syndrome, Laryngitis, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Myopathies, Ménière's disease, Narcolepsy, Nephritis, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pelvic inflammatory disease, Pemphigus vulgaris, Perivenous encephalomyelitis, Pernicious anaemia, Pharyngitis, Pleurisy, POEMS syndrome, Polyarteritis nodosa, Polymyalgia rheumatica, Polymyositis, Primary biliary cirrhosis, Primary sclerosing cholangitis, Progressive inflammatory neuropathy, Prostatitis, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Seborrheic dermatitis, Serum Sickness, Sinusitis, Sjogren's syndrome, Splenitis, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, thyroiditis, Tolosa-Hunt syndrome, Transverse myelitis, Ulcerative colitis, Undifferentiated spondyloarthropathy, Urticarial vasculitis, Vasculitis, Vitiligo, Wegener's granulomatosis, Familial Mediterranean fever (FMF), Hyperimmunoglobulinemia D with recurrent fever (HIDS), TNF receptor associated periodic syndrome (TRAPS), Muckle-Wells syndrome (CAPS, urticaria deafness amyloidosis), Familial cold urticarial, Neonatal onset multisystem inflammatory disease, Periodic fever, aphthous stomatitis, pharyngitis and adenitis (PFAPA syndrome), Blau syndrome, Pyogenic sterile arthritis, pyoderma gangrenosum, acne (PAPA), Deficiency of the interleukin-1-receptor antagonist (DIRA), Allergic reactions, Crohn's disease and Gout.

In certain aspects, the immune disorder is Rheumatoid arthritis, Systemic lupus erythematosus, Celiac disease, Crohn's disease, Inflammatory bowel disease, Sjogren's syndrome, Polymyalgia rheumatic, Psoriasis, Multiple sclerosis, Ankylosing spondylitis, Type 1 diabetes, Alopecia areata, Vasculitis, Temporal arteritis, Graves' disease, or Hashimoto's thyroiditis.

As used herein, "rheumatic disorder" refers to a disease or disorder characterized by the inflammation of a connecting or supporting structures of the body, mainly joints but also tendons, ligaments bones and muscles. Examples of rheumatic disorder include osteoarthritis, rheumatoid arthritis, fibromyalgia, systemic lupus erythematosus, gout, juvenile idiopathic arthritis, infectious arthritis, Lyme disease, Neisseria gonorrhoeae, psoriatic arthritis, spondlyoarthropathy polymyositis, bursitis, ankylosing spondylitis, reactive arthritis, Reiter's syndrome, scleroderma, systemic sclerosis, and polymyalgia rheumatic.

As used herein, the term "disease, disorder or condition of the central nervous system" is meant to refer to a disease, disorder or a condition which is caused by a genetic mutation in a gene that is expressed by cells of the central nervous system or cells that affect the central nervous system such that one of the effects of such a mutation is manifested by abnormal structure and/or function of the central nervous system, such as, for example, defective myelin. Such genetic defects may be the result of a mutated, non-functional or under-expressed gene in a cell of the central nervous system. As used herein, "central nervous system" should be construed to include brain and/or the spinal cord of a mammal. The term may also include the eye and optic nerve in some instances.

As used herein, "wound" refers to a injury or lesion to a living tissue, and includes puncture, abrasion, incision, laceration, burn and ulceration (diabetic and non-diabetic ulcer).

As used herein, "degenerative disease" refers to any disease affecting a tissue or an organ, and characterized by increasing deterioration over time. Many are related to aging but genetic, viral, prion induced and chemical induced diseases also exist. Example of degenerative disease include Alzheimer's disease (AD), Amyotrophic lateral sclerosis (ALS), Cancers, Charcot-Marie-Tooth disease (CMT), Chronic traumatic encephalopathy, Cystic fibrosis, cytochrome c oxidase deficiencies, degenerative Leigh syndrome, Ehlers-Danlos syndrome, Fibrodysplasia ossificans progressive, Friedreich's ataxia, Frontotemporal dementia (FTD), atherosclerosis, coronary artery disease, aortic stenosis, Huntington's disease, Infantile neuroaxonal dystrophy, Keratoconus (KC), Keratoglobus, Leukodystrophies, Macular degeneration (AMD), Marfan's syndrome (MFS), mitochondrial myopathies, Mitochondrial DNA depletion syndrome, Multiple sclerosis (MS), Multiple system atrophy, Muscular dystrophies (MD), Neuronal ceroid lipofuscinosis, Niemann-Pick diseases, Osteoarthritis, Osteoporosis, Parkinson's disease, Pulmonary arterial hypertension, prion diseases, Creutzfeldt-Jakob disease, fatal familial insomnia, Progressive supranuclear palsy, Retinitis pigmentosa (RP), Rheumatoid arthritis, Sandhoff Disease, Spinal muscular atrophy (SMA), Subacute sclerosing panencephalitis, Tay-Sachs disease and nerve degeneration.

As used herein "damaged or injured tissue" refers to any disease or disorder that affect the integrity and thus functionality of a tissue or organ. Examples of damaged or injured tissue related disease or disorder include adipose related disease or disorder, liver failure, myocardial infarction, heart attack, chronic heart failure, renal disease, kidney damage, retinal disease, retinal damage, retinal necrosis, lung injurie, intestinal disorder, spinal cord injurie, stroke, chronic obstructive pulmonary disease, and traumatic brain injury.

In certain aspects, the cells are used for the treatment of stroke, diabetes, arthritis, multiple sclerosis and chemotherapy-induced peripheral neuropathy; specific treatment protocols for those conditions are disclosed in the examples.

As used herein, "chemotherapy-induced peripheral neuropathy" or "CIPN" refers to the frequent, dose-dependent complication of anticancer drugs including platinums, taxanes, epothilones, vinca alkaloids, and newer agents, which causes numbness, tingling, or pain in the extremities and which is experienced by patients treated with a chemotherapeutic agent. The incidence of the neuropathy, its extend and the length of time the symptoms are experienced vary with the drug and its dose. CIPN presents clinically as deficits in sensory, motor, and sometimes autonomic function. Sensory disturbances range from mild tingling sensation to spontaneous burning pain and hypersensitivity to stimuli. The symptoms or pain may occur at any time during the course of chemotherapy, or even after termination. Symptoms may continue or worsen over weeks, months, or years, becoming a chronic neuropathy, and they may continue to be present after discontinuation of anti-cancer treatment.

The following usages of the cells are also contemplated: repairing or augmenting a tissue defect or injury site; repairing a damaged urinary tract tissue of a subject; repair and/or regeneration of musculoskeletal tissue; tissue repair implant; implantable biodegradable device containing a fibrous matrix; tissue reconstruction/repair of cartilage in vivo; bio-remodelable graft prostheses; gene therapy; repair or replacement or supporting of a section of a body tissue; use in producing a ligament or tendon; tissue engineering products for the treatment of human diseases and traumatic tissue injury repair; ex vivo produced anterior cruciate ligament; repair of skin defects; microspheres for application to wounds and/or lesions for accelerating wound healing and muscle regeneration; treatment of osteoporosis, osteolysis, improvement of bone implant adherence, augmentation of bone growth or bone repair, augmentation of cartilage repair, and augmentation of tissue production; formation of tubular tissue structures, like those of the gastrointestinal and genitourinary tracts, as well as cells; tissues for hernia repair and/or tendons and ligaments; human cellular non-structural tissue-derived multipotent adult stem cells; treatment of musculoskeletal diseases or disorders; treatment of articular cartilage fractures; and use with or in lieu of tissue fillers.

In many aspects, the cellular non-structural tissue is autologous or allogenic tissue. In various aspects, the subject is human. As used herein, the term "autologous" refers to any material derived from the same individual to which it is later to be re-introduced. Autologous tissues are from donors who are alive. However, live donors tissues could be harvested and used in other recipients, but the testing needed is typically not efficient economically. As used herein, the term "allogeneic" refers to any material derived from a donor other than the intended recipient. Allogeneic tissues may be harvested from donors who are not living (cadavers). One of the advantages of using cadaver as the source of non-structural tissue is the lower amount of red blood (non-nucleated) cells collected during the non-structural tissue harvest process, without impacting the amount of nucleated cells to be harvested. A further advantage is that the cadaver tissue can be stored for up to 6 days prior to the processing of the tissue. Methods of HLA tissue matching cells for infusion into immune compatible patients are well known in the art.

In various aspects, the cellular non-structural tissue is obtained by surgical excision or aspiration.

In one aspect, the administration is local or systemic. In many aspects, the PVF is administered by infusion, implantation or injection.

Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well as infusion, inhalation, and nebulization. The phrases "parenteral administration" and "administered parenterally" as used herein means modes of administration other than enteral and topical administration.

The concentrate and cleansed cells may be loaded into a delivery device, such as a syringe for placement into the recipient by either subcutaneous, intravenous, intramuscular, or intraperitoneal techniques. In other words, cells may be placed into the patient by any means known to persons of ordinary skill in the art, for example, they may be injected into veins for systemic or local delivery, into tissue (e.g., cardiac muscle, or skeletal muscle), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a preformed matrix.

The term "applicator," may be used herein, and is meant to refer to any device including, but not limited to, a hypodermic syringe, a pipette, a catheter and the like, for administering the compounds and compositions of the invention. Preferred embodiments include administration by needle or catheter, or by direct surgical implantation in association with additives such as a preformed matrix.

In other aspects, the method further includes administering tissue filler, non PVF-derived cells, tissue, tissue fragment, demineralized bone, growth factor, drug, biologically active compound, biologically inert compound, scaffold, matrix, pharmaceutical agent, polynucleotide encoding a therapeutic agent or a combination thereof.

In many aspects, the tissue filler, non PVF-derived cells, tissue, tissue fragment, demineralized bone, growth factor, drug, biologically active compound, biologically inert compound, scaffold, matrix, pharmaceutical agent, polynucleotide encoding a therapeutic agent or combination thereof is administered prior to, simultaneously with, or after the administration of the PVF.

In some aspects administration can be in combination with one or more additional agents. The phrases "combination therapy", "combined with" and the like refer to the use of more than one medication or treatment simultaneously to increase the response. The composition of the present invention might for example be used in combination with other drugs or treatment in use to treat the disease, disorder or condition. Such therapies can be administered prior to, simultaneously with, or following administration of the composition of the present invention. The pharmaceutical composition may also contain other therapeutic agents, and may be formulated, for example, by employing conventional vehicles or diluents, as well as pharmaceutical additives of a type appropriate to the mode of desired administration (for example, excipients, preservatives, etc.) according to techniques known in the art of pharmaceutical formulation.

Depending on the condition being treated, these pharmaceutical compositions may be formulated and administered systemically or locally. Techniques for formulation and administration are generally known in the art. For injection, the pharmaceutical compositions of the invention may be formulated in aqueous solutions, preferably in physiologically compatible buffers such as Hanks' solution, Ringer's solution, or physiologically buffered saline.

In other aspects, the method further includes concentrating the isolated PVF.

The isolated cells can optionally be washed with any suitable physiologically-compatible solution, such as phosphate buffer saline (PBS) or normal saline. However, using the exemplified methods, washing is not required. The cellular fraction may be infused into a subject or may be further concentrate and cleansed into a pellet by any suitable method, such as centrifugation, and retained for further processing. If desired, the PVF may be resuspended and can be further washed in physiologically compatible buffer, centrifuged, and resuspended one or more successive times to achieve greater purity. During centrifugation heavier particles settle to bottom and lighter to the top, which helps concentrating the cells and re-suspending the cells at a desired concentration. The cells may also be plated and cultured.

In various aspects, the PVF includes about 10-100 million perivascular cells and/or pericytes. In one aspect, the PVF includes about 50-100 million perivascular cells and/or pericytes. In many aspects, the perivascular cells and/or pericytes concentration in the PVF is about 1-5 million cells per milliliter.

In an additional embodiment, the invention provides a method for improving a tissue in a subject including administering to the tissue a pericyte vascular fraction (PVF), wherein the PVF is derived by a method including sonicating a cellular non-structural tissue, wherein the sonication is indirect sonication, and wherein the PVF further includes a pharmaceutically acceptable carrier, diluent and/or excipient.

In many aspects, improving the tissue includes reconstructing, regenerating, augmenting the volume of, and healing the tissue, or any combination thereof.

As used herein, the improvement of a tissue is to be understood as a cosmetic procedure, which include the administration of a "cosmetically or aesthetically effective amount" of the PVF composition, which refers to the amount of PVF composition which is sufficient to provide a cosmetically or aesthetically beneficial effect to the subject to which the PVF composition is administered. Such effect include skin rejuvenation, enhancement in plumpness or volume or appearance of the treated tissue. Also, as used herein, a "cosmetically effective amount" is the amount of cells which is sufficient to provide a beneficial effect to the subject to which the cells are administered.

In various aspects, the tissue is a skin, a facial tissue, a buttock, a muscle, an oral tissue breast, musculoskeletal tissue, neurological tissue, or cellular tissue, and the facial tissue is a lip and the oral tissue is a gum. In certain aspects, the tissue includes a wrinkle, a wound or a scar. In some aspects, the tissue is allogenic.

In other aspects, the method further includes administering tissue filler, non PVF-derived cells, tissue, tissue fragment, demineralized bone, growth factor, drug, biologically active compound, biologically inert compound, scaffold, matrix, pharmaceutical agent, polynucleotide encoding a therapeutic agent or a combination thereof. In one aspect, the PVF further included a pharmaceutically acceptable carrier, diluent and/or excipient.

In another embodiment, the invention provides a method of processing a cellular non-structural tissue including sonicating the tissue, wherein the sonication is indirect sonication.

As used herein "processing a tissue" refers to the minimal manipulation of the tissue that are executed after the collection of said tissue from a donor. The processing of the tissue as intended in the present invention is realized in sterile conditions and includes the ultrasonication of the tissue and optional washes as disclosed below in the examples.

As used herein "indirect sonication", "indirectly sonicating" and the like refer to the presently disclosed method for processing cellular non-structural tissues, where the sonication of the tissue to be processed id performed from a distance to the sonication device. As previously described, the sonication device is not critical to the invention; any device capable of generating ultrasounds waves at a 15-50 kHz frequency, and capable of disrupting a tissue integrity without altering the cells is acceptable. Such devices include sonicator such as those with a sonication head.

In one aspects, intact cells are isolated following the sonication. The processing of the tissue according to the present invention allows the isolation of high yields of intact and viable cells from the cellular non-structural tissue.

In many aspects, the cellular non-structural tissue is cadaver tissue. In various aspects, the tissue is stored for 0 to 96 hours prior to processing. In other aspects, the tissue is stored at about 0-7° C. In one aspect, the tissue is stored at 3° C.

In one aspect, the distance between the tissue and an ultrasonic cavitation head is about 3-4 millimeters. In another aspect, the sonication is performed at about 15-50 kHz. In one aspect, the sonication is performed at about 20 kHz. In yet another aspect, the tissue is sonicated for about 5-15 minutes. In various aspects, the tissue is maintained in a container surrounded by water. In one aspect, the water is maintained at the same level as the tissue. In certain aspects, the water temperature is about 0-40° C. In other aspects, the water temperature is about 20° C.

In many aspects, the container further includes a physiologically compatible solution. By "physiologically compatible solution" it is meant that the solution in which the tissue is processed prevents drastic changes in osmotic pressure in the cells and therefore does not alter the cells osmolality. Examples of physiologically compatible solution are well known in the art and include, but are not limited to, saline solution or PBS.

In an additional embodiment, the invention provides an apparatus for processing a cellular non-structural tissue including a first container including an ultrasonic cavitation head, a second container, and a weighted cap adhering to the second container.

In one aspect, the second container includes cellular non-structural tissue. In another aspect, the first container additionally includes water, and the water is at the same level as the tissue in the second container. In yet another aspect, the water in the first container is circulating. In an additional aspect, the water temperature is about 20° C.

As used herein, "container" refers without any distinction to the means used to contained and to hold the sonication device and to the mean used to contained and to hold the tissue. The container that holds the tissue can be of any material that can be made sterile, and that would allow the proper transfer of the ultrasound waves generated by the sonication device through the container and into the tissue. A non-limiting example of such container include a sonication bottle. The size of the container is not limiting and should be chosen according to the amount of tissue to be processed. The container that holds the sonication device and the container that holds the tissue is a larger container that can safely be filled with water. The temperature of said water must be monitored and controlled so that a constant temperature can be applied to the tissue throughout the entire time of processing. An additional way of maintain a constant temperature of the tissue is to ensure that the water is at the same level as the tissue in the second container. Non-limiting example of such container includes a water bath, with a circulating water system.

As used herein, "weighted cap" refer to the cap of the first larger container, used to keep the temperature in said container heaven. This cap is weighted and is adhering to the second container to that it can prevent any movement of the containers that could be generated during the processing.

In various aspect, the frequency of ultrasounds generated by the cavitation head is about 15-50 kHz. In many aspects, the frequency of ultrasounds generated by the cavitation head is about 20 kHz.

In one aspect, the distance between the second container and the ultrasonic cavitation head is about 3-4 millimeters.

The apparatus of the present invention is design to process tissue through indirect sonication. As previously discussed, this process requires that the sonication device and the tissue are separated from each other during the process, such that the sonication occurs only through the propagation of the ultrasonic waves from the device to the tissue (through the water and the container holding the tissue).

Presented below are examples discussing PVF and PVCs as well as method of producing them, contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Isolation of Pericyte Vascular Fraction (PVF) by Ultrasonic Cavitation

Using indirect ultrasonic cavitation, a cellular non-structural tissue sample is ultrasonicated, which results in a perivascular fraction (PVF) and from which pericytes and perivascular cells (PVCs) are isolated. The general steps of the isolation method are illustrated in FIG. 1.

The following laboratory protocol is used to process cellular non-structural tissue and derive a pericyte vascular fraction containing cells from cellular non-structural tissue (e.g., collected from patients). It is to be understood that the protocol is exemplary and that the specifics may be modified by a skilled artisan in order to be further optimized.

The tissue is surgically harvested from a donor. The non-structural tissue, i.e. the subcutaneous fluid surrounding adipose tissue, and including cells of interest is collected from the donor using a 2.1 mm cannula. This small cannula (as opposed to a 4 mm cannula usually used during lipoaspiration, for adipose tissue removal) is used to allow for a more targeted collection of fluid rather than structural element such as adipose tissue, and for a reduce amount of red blood cells (non-nucleated cells) harvested. A limited amount of structural tissue (adipose tissue) is collected with the fluid, but the adipose tissue is decanted and removed prior to further processing. The harvested tissue can be stored, over a period of 96 hours, at a range of 32-44 degrees, with 37° F. (3° C.) being the optimal temperature.

Figure 2:
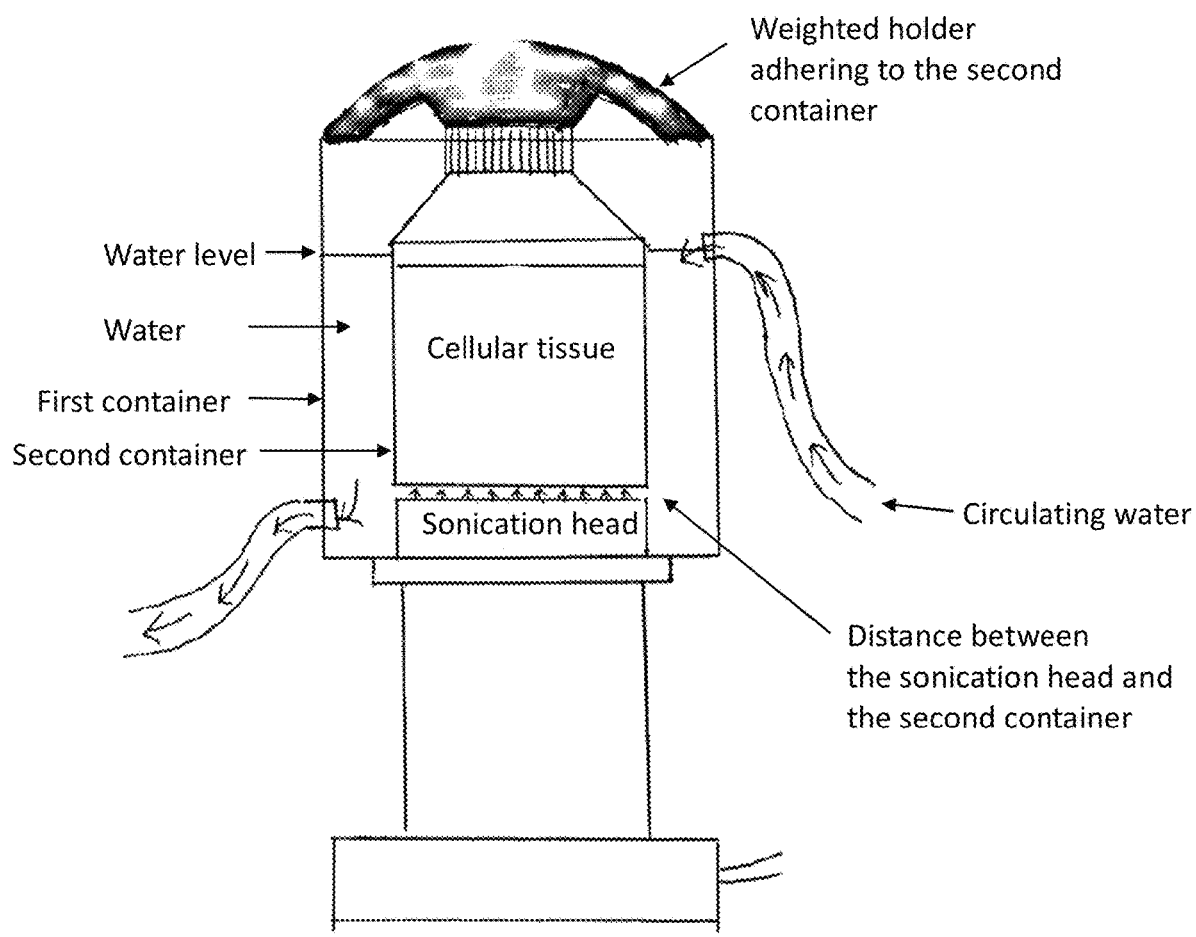
FIG. 2 is a schematic representation of the apparatus used for the isolation of perivascular cells from a cellular non-structural tissue.

The procedure is performed in sterile conditions, using a laminar flow hood (positive pressure recirculating sterile isolator hood, PPH) properly turned on (with gauge checked), and set up with sterile disposable drapes and tubes. As illustrated in FIG. 2, the sonication head is attached with a water bath encasing the head, a weighted holder is adhering to the bottle containing the sample and is placed into the bath with the tissue in the bottle to hold the bottle containing the sample. No sonication probe is used. The particular ultrasonic cavitation device used is not critical to the invention. The device used is the Qsonica Q500S sonicator with recirculating chiller device which is a technologically advanced high intensity ultrasonic processor with Oasis 180 temperature control system integrated to control temperature changes.

The first step is to harvest capillary perivascular cells (CPVCs). The cellular non-structural tissue is placed into a sonication bottle and the CPVCs, collected in the decanted liquid, are placed into tubes using syringes. The tissue is optionally washed with any suitable physiologically compatible solution, such as phosphate buffer saline (PBS) or normal saline, but washing is not required.

The sonication bottle is removed from the PPH and placed into the sonicator. The sonication bottle is placed in holder and then over the sonicating head. Sonication is performed at 90% amplitude for 5 minutes (intervals of 59 second pulses per 10 seconds of rest). After treatment, the sonication bottle is allowed to settle, and the dissociated cellular non-structural tissue leads to three different layers. The top layer is a free lipid (fat) layer; the middle layer includes the lattice and pericyte aggregates; and the bottom layer or cell pellet contains the perivascular cells (PVCs).

During the indirect sonication, the distance between the tissue and the sonicating head is up to 20 mm with an optimum distance of 3-4 mm. The ultrasonic cavitation time used ranges from about 1 minute to about 9 hours, with an optimal duration of about 5-15 minutes. Those optimal duration and distance are found the best to concentrate and cleanse most of the pericytes in the cellular non-structural tissue and blood cells under conditions that release the PVF containing pericyte and PVCs, precursors and other cell types contained therein without adversely affecting the viability and number of these cells from different samples. The temperature of the water in the water bath ranges from 0 to 40° C., with an optimum temperature of 20° C. with circulating water.

After sonication, the sonication bottle is sterilized and placed back in the PPH. The cellular fraction of the bottom layer is removed and separated into tubes which are filled with saline. Using a premiere low speed centrifuge, both CPVCs and PVCs containing tubes are centrifuged at 3000 rpms for 6 minutes. After centrifugation, the material is layered with the fat on the top and the pellets on the bottom of the tubes. All the fat layer and most of the liquid are decanted, the pellets are resuspended and combined into one tube. At this point, if greater purity is desired, the cells can be washed in a physiologically compatible buffer, centrifuged, and resuspended one or more successive times.

Final samples are filtered using a 60 μM SteriFlip cell filtration device and are ready to be used for storage or for infusion.

For storage, final sample tube are centrifuged at 3000 rpms for 6 minutes and all liquid is decanted. The pellet is resuspended in a freezing agent, transferred into a cryovial and placed in the freezer for storage (see Example 16 for further details).

Example 2

Evaluation of the Number of Perivascular Cells (PVCs)

The number of cells isolated from a sample is evaluated using a Luna Stem Cell Counter.

100 microliters of the final filtered PVC samples are removed for testing prior to use or preparation for storage. The sample is diluted in saline as the diluent. Four microliters of Acridine Orange/Propidium Iodide dye are mixed with 36 microliters of diluted sample. Ten microliters of the mixture are pipetted into each side of a slide. By taking into account the multiplication factor to adjust for the dilution, the cell counts are assessed and the results recorded. The average of two readings is determined (nucleated cells, non-nucleated cells, and percent of viability) and saved for each sample. The process is repeated for 2 more slides for a total of 3 slides per sample.

Example 3

Isolation of Pericyte Vascular Fraction (PVF) From a Cadaver

For allogenic graft, where the tissue was collected from a donor, cadavers were used as a suitable source of cellular non-structural tissue.

Any inadvertently collected structural adipose tissue was decanted and removed from the sample prior to the processing of the sample. The sonication bottle containing the harvested cellular non-structural tissue was placed in holder and then over the sonicating head.

During the indirect sonication, the distance between the tissue and the sonicating head was 3-4 mm. The temperature of the water in the water bath was 20° C. with circulating water.

Six syringes containing approximately 226 milliliters were collected from a cadaver and processed on day 2 (48 hours after death). The content of all 6 syringes was put into a sonication bottle, mixed and distributed into conical tubes to perform 3 individual tests, each test contained approximately 75 ml. Test 1A was performed on the same day (day 2, 48 hours after death). Test 1B was performed on day 3 (72 hours after death) and test 1C was performed 6 days after death. For all 3 tests the entire sample was sonicated, separated into 2 conical tubes and filled to 50 ml mark with saline (approximately 25 ml total of saline). The sample was then centrifuged, the fat layer was decanted off each tube, the tubes were combined into one tube and the sample was filtered.

Approximately 300 μl was taken from the sample, and appropriate dilutions were made for cell count (as described above in Example 2). As illustrated is Table 1, when the cellular non-structural tissue was processed 48 after death, among the 2.77-2.93E+07 cells retrieved, 6.05-9.81E+04 cells were nucleated, with a cell viability ranking from 88 to 100%.

TABLE 1

Cell counts and cell viability obtained with a cellular non-structural tissue processed 48 h after death

| Name | Total Cell | Nucleated Cell | Non-Nucleated Cell | Viability of Nucleated Cell | Dilution |
|---|---|---|---|---|---|
| t1-1a-3b(1) | 3.16E+06 | 2.45E+03 | 3.16E+06 | 100.00% | 25% |
| t1-1a-3a | 7.24E+06 | 4.90E+03 | 7.24E+06 | 100.00% | 25% |
| t1-1a-2a | 7.59E+06 | 1.72E+04 | 7.58E+06 | 85.70% | 25% |
| t1-1a-2b(1) | 7.60E+06 | 1.96E+04 | 7.58E+06 | 75.00% | 25% |
| t1-1a-25per-b | 7.72E+06 | 2.45E+04 | 7.70E+06 | 80.00% | 25% |
| t1-1a-25per-a | 8.29E+06 | 2.21E+04 | 8.27E+06 | 88.90% | 25% |
| Average | 2.77E+07 | 6.05E+04 | 2.77E+07 | 88.27% | |
| t1-1a-3b | 1.31E+06 | 2.45E+03 | 1.31E+06 | 100.00% | 5% |
| t1-1a-2b | 1.52E+06 | 7.36E+03 | 1.52E+06 | 100.00% | 5% |
| t1-1a-b-10per | 1.57E+06 | 4.90E+03 | 1.57E+06 | 100.00% | 5% |
| Average | 2.93E+07 | 9.81E+04 | 2.93E+07 | 100.00% | |

In order to assess the impact of freezing/thawing process on cell counts and viability, the final product obtained 48 h after death was frozen. The sample (1A) was centrifuged again after collecting 300 μl for cell counts. Most of the liquid was decanted to leave approximately 5 ml. The sample was mixed and 10 ml of freezing agent was used. The sample was divided into 5 vials with a volume of 2 ml each, and the remaining of the suspension was frozen into a sixth vial, containing just over 1 ml. Four days after freezing, the sixth vial was thawed for a cell count. As illustrated in Table 2, after freezing and thawing, up to 2.93E+07 cells were recovered in a little over 1 ml; among those, up to 9.81E+04 were nucleated cells, with a viability ranking from 85 to 100%.

TABLE 2

Cell counts and cell viability obtained after freezing and thawing

| Name | Total Cell | Nucleated Cell | Non-Nucleated Cell | Viability of Nucleated Cell | Dilution |
|---|---|---|---|---|---|
| t1-1a-thaw-25-3b | 2.67E+06 | 2.70E+04 | 2.64E+06 | 90.90% | 25% |
| t1-1a-thaw-25-2b | 3.15E+06 | 1.23E+04 | 3.14E+06 | 80.00% | 25% |
| t1-1a-thaw-25-2a | 3.24E+06 | 4.90E+03 | 3.24E+06 | 100.00% | 25% |
| t1-1a-thaw-2-b | 3.35E+06 | 7.36E+03 | 3.35E+06 | 100.00% | 25% |
| t1-1a-thaw-25er-a | 3.68E+06 | 2.70E+04 | 3.65E+06 | 54.50% | 25% |
| Average | 1.29E+07 | 6.28E+04 | 1.28E+07 | 85.08% | |
| 1A | 2.77E+07 | 6.05E+04 | 2.77E+07 | 88.27% | 25% |
| 1A | 2.93E+07 | 9.81E+04 | 2.93E+07 | 100.00% | 5% |
| 1A | 1.29E+07 | 6.28E+04 | 1.28E+07 | 85.08% | 25% |

As shown in Table 3, when the cellular non-structural tissue was processed 72 h after death, among the 3.39-6.57E+07 cells retrieved, 6.13E+04-1.17E+05 cells were nucleated, with a cell viability ranking from 69 to 91%.

TABLE 3

Cell counts and cell viability obtained with a cellular non-structural tissue processed 72 h after death

| Name | Total Cell | Nucleated Cell | Non-Nucleated Cell | Viability of Nucleated Cell | Dilution |
|---|---|---|---|---|---|
| t1-1b-10per-3b | 6.16E+06 | 4.90E+03 | 6.16E+06 | 100.00% | 10% |
| t1-1b-10per-3a | 6.50E+06 | 1.96E+04 | 6.48E+06 | 87.50% | 10% |
| t1-b1-10per-2b | 6.35E+06 | 9.81E+03 | 6.34E+06 | 75.00% | 10% |
| t1-1b-10per-a | 7.26E+06 | 1.23E+04 | 7.25E+06 | 100.00% | 10% |
| Average | 6.57E+07 | 1.17E+05 | 6.56E+07 | 90.63% | |
| rt-1b-10per-3a | 3.73E+06 | 2.45E+03 | 3.73E+06 | 0.00% | 10% |
| rt-1b-10per-2a | 2.69E+06 | 2.45E+03 | 2.68E+06 | 100.00% | 10% |
| rt-b1-10pr-b | 3.39E+06 | 9.81E+03 | 3.38E+06 | 100.00% | 10% |
| rt-1b-10per-a | 3.75E+06 | 9.81E+03 | 3.74E+06 | 75.00% | 10% |
| Average | 3.39E+07 | 6.13E+04 | 3.38E+07 | 68.75% | |

As illustrated in Table 4, when the cellular non-structural tissue was processed 6 days after death, among the 9.11E+07 cells retrieved, 6.87E+04 cells were nucleated, with a cell viability of 100%.

TABLE 4

Cell counts and cell viability obtained with a cellular non-structural tissue processed 6 days after death

| Name | Total Cell | Nucleated Cell | Non-Nucleated Cell | Viability of Nucleated Cell | Dilution |
|---|---|---|---|---|---|
| t1-1c-10-3a | 8.15E+06 | 4.90E+03 | 8.14E+06 | 100.00% | 10% |
| t1-1c-10-2b | 8.61E+06 | 7.36E+03 | 8.60E+06 | 100.00% | 10% |
| t1-1c-10-2a | 9.85E+06 | 7.36E+03 | 9.84E+06 | 100.00% | 10% |
| t1-1c-10per-b | 9.08E+06 | 9.81E+03 | 9.07E+06 | 100.00% | 10% |
| t1-1c-10per-a | 9.87E+06 | 4.90E+03 | 9.86E+06 | 100.00% | 10% |
| Average | 9.11E+07 | 6.87E+04 | 9.10E+07 | 100.00% | |

It was also found that collecting non-structural tissue on a cadaver donor resulted in lower yields of non-nucleated cells.

Example 4

Characterization and Isolation of Perivascular Cells (PVCS)

After a cellular non-structural tissue containing cells is treated using the ultrasonic cavitation device the concentrated pericytes (at the top of the composition) is removed and the remaining pericyte or pericyte vascular fraction from the concentrated cells is further isolated or assayed (such as by flow cytometry) for the presence of desired cell types including precursor cells. This can be obtained by known methods including flow cytometry or fractionation into different cell types using fluorescence activated call sorting (FACS), e.g., based on cell surface antigens which are specific to perivascular cells or other cell lineages contained in cellular non-structural tissue. Suitable antigens and markers are disclosed herein.

Cell contained therein and markers isolatable from cellular non-structural tissue according to the invention included by way of example pericyte cells, hematopoietic cells, hematopoietic cells, platelets, Kupffer cells, osteoclasts, megakaryocytes, granulocytes, NK cells, precursor or progenitor cells, CD34+ cells or pericyte cells, (typically found in umbilical cord), CD29+ cells, CD166+ cells, Thy-1+ or CD90+ cells, CD44+ cells, immune cells such as monocytes, leukocytes, lymphocytes, B and T cells, NK cells, macrophages, neutrophil leukocytes, neutrophils, neutrophil granulocytes, and the like including immune and other cells that express one or more of the following markers: CD3, CD14 (macrophage marker), CD19, CD20 (B cell marker), CD29 (integrin unit) CD31 (endothelial, platelet, macrophage, Kupffer cell, granulocyte, T/NK cells, lymphocytes, megakaryocytes, osteoclasts, neutrophils, et al.), CD44 (Hyaluronic acid receptor) CD45 (B and T cell marker), C56, CD73 (lymphocyte differentiation marker), CD105 et al. Also, it includes cells expressing any of the markers disclosed in this application or any combination of these markers.

Perivascular cells that express at least one protein selected from the group consisting of CD13, CD29, CD34, CD36, CD44, CD49d, CD54, CD58, CD71, CD73, CD90, CD105, CD106, CD151 and SH3, or CD13, CD29, CD34, CD36, CD44, CD49d, CD54, CD58, CD71, CD73, CD90, CD105, CD106, CD151 and SH3 and/or CD31, CD45, CD117 and CD146 and do not express CD56 can thus be isolated.

Cells that express at least one protein selected from the group consisting of CD3, CD4, CD14, CD15, CD16, CD19, CD33, CD38, CD56, CD61, CD62e, CD62p, CD69, CD104, CD135 and CD144, and do not express CD3, CD4, CD14, CD15, CD16, CD19, CD33, CD38, CD56, CD61, CD62e, CD62p, CD69, CD104, CD135 and CD144 or express CD49d and do not express CD56 can also be isolated.

Somatic tissue cells can be isolated from the subject pericyte or pericyte vascular fraction by fractionation using fluorescence activated call sorting (FACS) with unique cell surface antigens to isolate specific subtypes of cells (such as adipose derived cells) for injection into recipients following expansion in vitro. As stated above, cells can be derived from the individual to be treated or from a matched donor. Those having ordinary skill in the art can readily identify matched donors using standard techniques and criteria.

Example 5

Processing of Perivascular Cell (PVC) Samples

While the PVCs derived from cellular non-structural tissue may be used directly for treatment, cells are also alternatively prepared in compositions that include other agents.

The active cells that have been concentrate and cleansed, as described above, may be administered to a patient without further processing, or may be administered to a patient after being mixed with other tissues or cells. the concentrate and cleansed active cells (e.g., cells or precursor cells) can for example be mixed with one or more units of cellular non-structural tissue that has not been similarly processed. Thus, by practicing the methods of the invention, a composition including cellular non-structural tissue with an enhanced concentration of active cells may be administered to the patient. The PVCs that are concentrated and cleansed by the method previously described, are to be administered to patient after being mixed with other tissues or cells. The PVCs are, for example, mixed with one or more units of cellular non-structural tissue that has not been similarly processed. The volumes of the various units of cellular non-structural tissue may be different. For example, one volume may be at least 25% greater than the volume of another unit of cellular non-structural tissue. Furthermore, one volume may be at least 50%, such as at least 100%, and even 150% or more greater than the volume of another unit of cellular non-structural tissue. In addition, the desired composition may be obtained by mixing a first unit of cellular non-structural tissue with the concentrate and cleansed PVCs, which may be a cell pellet, with one or more other units of cellular non-structural tissue. These other units may not have an increased concentration of cells, or in other words, may have an active cell concentration less than that contained in the first unit of cellular non-structural tissue. One or more of the units may be cryopreserved material that contains, for example, an increased concentration of active cells.

The PVCs are applied in combination with non PVF-derived cells, tissue or tissue fragments, demineralized bone, growth factors such as insulin, drugs such as members of the thiaglitazone family, biologically active or inert compounds, resorbable plastic scaffolds, or other additive intended to enhance the delivery, efficacy, tolerability, or function of the population.

The PVCs can be mixed with unprocessed fragments of cellular non-structural tissue and placed back into the recipient using a very large gauge needle or harvest cannula. Transfer of autologous PVCs without supplementation with processed cells is a common procedure in plastic and reconstructive surgery. However, results can be unpredictable as the transferred material tends to rapidly reabsorb resulting in an unstable graft. Cellular non-structural tissue-derived cells of the invention that are, for example, substantially depleted of mature pericytes may provide an environment that supports prolonged survival and function of the graft.

The PVCs can be placed into the recipient and surrounded by a resorbable plastic sheath such as that manufactured by MacroPore Biosurgery, Inc. In this setting, the sheath prevents prolapse of muscle and other soft tissue into the area of a bone fracture thereby allowing the emplaced processed cellular non-structural tissue-derived cells to promote repair of the fracture. In this aspect, the beneficial effect might be enhanced by supplementation with additional components such as pro-osteogenic protein growth factors or biological or artificial scaffolds.

The PVCs can also be administered to a patient with one or more cellular differentiation agents, such as cytokines and growth factors.

The PVCs or composition may in addition further contain an additional pharmaceutical or agent, or alternatively a polynucleotide that encodes for a therapeutic agent or for an inhibiting nucleic acid. Examples of nuclear acids include, a ribozyme, an antisense oligonucleotide, a double stranded RNA, a double-stranded interfering RNA (iRNA), a triplex RNA, an RNA aptamer, and at least a portion of an antibody molecule that binds to the gene product and inhibits its activity.

Example 6

Contemplated Usages of Isolated Perivascular Cells (PVCs)

The present invention contemplates any known usage of the subject adipose derived PVCs or PVF or and precursor cells purified or derived therefrom such as by induced differentiation.

For example U.S. Pat. No. 7,875,296 by Binette et al discloses conformable tissue implant for use in repairing or augmenting a tissue defect or injury site that may contain cells. The tissue implant contains a tissue carrier matrix including a plurality of biocompatible, bioresorbable granules and at least one tissue fragment in association with the granules.

U.S. Pat. No. 7,875,276 by Kropp discloses the use of stem cells for repairing a damaged urinary tract tissue of a subject.

U.S. Pat. No. 7,625,581 discloses the use of and precursor cells in tissue scaffolds suitable for use in repair and/or regeneration of musculoskeletal tissue when implanted in a body.

U.S. Pat. No. 7,316,822 by Binette also discloses a tissue repair implant comprising: a tissue carrier matrix comprising a plurality of biocompatible, bioresorbable granules and at least one tissue fragment in association with the tissue carrier matrix, the at least one tissue fragment having an effective amount of viable cells that can migrate out of the tissue fragment and populate the tissue carrier matrix, wherein the tissue carrier matrix is in the form of an injectable suspension, and wherein an average maximum outer diameter of the granules is in a range of about 150 to about 600 um.

U.S. Pat. No. 7,299,805 by Benutti et al discloses a method of implanting or precursor cells into a body of a patient, said method comprising the steps of: providing a support structure, harvesting a polysaccharide-based modified biofilm from bacteria, attaching viable cells for implantation to the support structure with the polysaccharide-based modified biofilm, and connecting one portion of a blood vessel in the patient's body with a first portion of the support structure, and connecting another portion of a blood vessel in the patient's body with a second portion of the support structure.

U.S. Pat. No. 7,192,604 by Brown et al and assigned to Ethicon discloses an implantable biodegradable device containing a fibrous matrix, the fibrous matrix being constructed from fibers A and fibers B, wherein fibers A biodegrade faster than fibers B, fibers A and fibers B are present in relative amounts and are organized such that the fibrous matrix is provided with properties useful in repair and/or regeneration of mammalian tissue, and which may contain stem cells or precursor cells.

U.S. Pat. No. 7,078,230 by Wilkinson et al assigned to Artecel, Inc discloses the use of pluripotent cells generated from cellular non-structural tissue-derived stem cells that have been induced to express at least one phenotypic characteristic of a neuronal, astroglial, hematopoietic progenitor, or hepatic cell and the use thereof in therapy or tissue reconstruction.

U.S. Pat. Nos. 7,033,587, 6,841,150, and 6,429,013 by Halvorsen and discloses to Artecel, Inc teach methods and compositions for directing stem cells cultivated in vitro to differentiate into cells of the chondrocyte lineage. They also teach the use of the differentiated chondrocytes for the therapeutic treatment of a number of human conditions and diseases including repair of cartilage in vivo is disclosed.

U.S. Pat. No. 6,986,735 by Abraham et al and discloses to Organogenesis teaches methods of making bioremodelable graft prostheses prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or use in a mammalian host. These prostheses may contain pericyte cells or precursor cells.

Still further, U.S. Pat. No. 6,991,787 by Greenberger discloses the use of stem cells for use in gene therapy.

U.S. Pat. No. 7,011,328 by Barofsky discloses a method of effecting repair or replacement or supporting a section of a body tissue using tropoelastin, preferably crosslinked tropoelastin and specifically to provide a tropoelastin biomaterial suitable for use as a stent, for example, a vascular stent, or as conduit replacement, as an artery, vein or a ureter replacement. The tropoelastin biomaterial itself can also be used as a stent or conduit covering or coating or lining and may comprise stem cells or precursor cells.

U.S. Pat. No. 6,902,932 by Altman et al, assigned to Tissue Regeneration, Inc. and the Trustees of Tufts College describes a novel silk-fiber-based matrix having a wire-rope geometry for use in producing a ligament or tendon, particularly an anterior cruciate ligament, ex vivo for implantation into a recipient in need thereof, which may seeded with pluripotent cells that proliferate and differentiate on the matrix to form a ligament or tendon ex vivo. Also disclosed is a bioengineered ligament comprising the silk-fiber-based matrix seeded with pluripotent cells that proliferate and differentiate on the matrix to form the ligament or tendon.

U.S. Pat. No. 6,555,374 by Gimble et al, assigned to Artecel Sciences, Inc. discloses compositions for the differentiation of stomal cells from cellular non-structural tissue into hematopoietic supporting stem cells and myocytes of both the skeletal and smooth muscle type. The cells produced by the methods are useful in providing a source of fully differentiated and functional cells for transplantation and development of tissue engineering products for the treatment of human diseases and traumatic tissue injury repair.

U.S. Pat. No. 6,287,340 by Altman et al discloses anterior cruciate ligament ex vivo produced by seeding pluripotent cells in a three dimensional matrix, anchoring the seeded matrix by attachment to two anchors, and culturing the cells within the matrix under conditions appropriate for cell growth and regeneration, while subjecting the matrix to one or more mechanical forces via movement of one or both of the attached anchors.

U.S. Pat. No. 6,284,284 by Naughton discloses compositions containing natural human extracellular matrices which may contain adipose derived cells for the repair of skin defects using natural human extracellular matrix by injection.

U.S. Pat. No. 6,086,863 by Ritter et al, and assigned to Polyheal Ltd. discloses therapeutic compositions of microspheres for application to wounds and/or lesions for accelerating wound healing and muscle regeneration that may comprise adipose derived pluripotent cells.

U.S. Pat. No. 6,082,364 by Balian et al, and assigned to Musculoskeletal Development Enterprises discloses the use of adipose derived pluripotent-like cells for systemic administration to treat osteoporosis, osteolysis, improve bone implant adherence, augment bone growth or bone repair, augment cartilage repair, and augment tissue production for, e.g., breast augmentation, and the like.

U.S. Pat. Nos. 6,022,743, 5,858,721, 5,842,477 and 5,785,964, all by Naughton et al and assigned to Advanced Tissue Sciences, Inc. disclose a stem cell-based three-dimensional cell culture system which can be used to culture a variety of different cells and tissues in vitro for prolonged periods of time. They disclose the use of this three-dimensional culture to form tubular tissue structures, like those of the gastrointestinal and genitourinary tracts, as well as cells; tissues for hernia repair and/or tendons and ligaments; etc.

U.S. Pat. No. 5,902,741 by Purchio et al relates to a method of stimulating the proliferation and appropriate cell maturation of a variety of different cells and tissues in three-dimensional cultures in vitro using TGF-beta. in a culture medium containing pericyte cells, including, but not limited to, chondrocytes, chondrocyte-progenitors, fibroblasts, fibroblast-like cells inoculated and grown on a three-dimensional framework in the presence of TGF-.beta. This three-dimensional system, allows for the proliferating cells mature and segregate properly to form components of adult tissues analogous to counterparts in vivo.

U.S. Pat. No. 5,478,739 by Slivka et al also describes a three-dimensional cell culture system in which stem cells are grown on a three-dimensional matrix while cycling the cultures between metabolically favorable and metabolically unfavorable (but noncytotoxic) conditions and produces an overall structure that more closely resembles naturally occurring tissue.

U.S. Pat. No. 7,807,461 by Kang et al relates to human cellular non-structural tissue-derived multipotent adult stem cells. which can be maintained in an undifferentiated state for a long period of time by forming spheres and have high proliferation rates, as well as methods for isolating and maintaining the adult cells, and methods for differentiating the multipotent adult cells into nerve cells, pericytes, cartilage cells, osteogenic cells and insulin-releasing pancreatic beta-cells. Also, they teach the use thereof for treating osteoarthritis, osteoporosis and diabetes and for forming breast tissue, which contain the differentiated cells or the adult cells.

U.S. Pat. Nos. 7,771,716 7,651,684 7,585,670 7,514,075, and 7,470,537, all by Hedrick et al and assigned to Cytori Therapeutics, Inc. describe the use of regenerative cells present in cellular non-structural tissue to treat patients, including patients with musculoskeletal diseases or disorders. Methods of treating patients include processing cellular non-structural tissue to deliver a concentrate and cleansed amount of regenerative cells obtained from the cellular non-structural tissue to a patient. The methods are practiced in a closed system so that the stem cells are not exposed to an external environment prior to being administered to a patient.

U.S. Pat. Nos. 7,687,059 7,501,115 and 7,473,420, all by Fraser et al and assigned to Cytori Therapeutics, Inc. discloses the use of and other cells present in processed lipoaspirate tissue to treat patients. Methods of treating patients including processing cellular non-structural tissue to deliver a concentrate and cleansed amount of cells obtained from the cellular non-structural tissue to a patient are disclosed.

U.S. Pat. No. 7,531,355 by Rodriguez et al and assigned to The Regents of the University of California describes a purified or isolated population of adipose derived cells (PVC'S) that can differentiate into a cell of the leiomyogenic lineage, e.g., smooth muscle or skeletal muscle or into a lineage selected from the group consisting of osteogenic, adipogenic, chondrogenic, myogenic and neurons. They describe use of an effective amount of the cells being applied to the area or tissue requiring therapy, e.g., bladder. In addition, for total tissue substitution, three dimensional scaffolds are taught using PLGA, PCL, or other materials. These scaffolds can be seeded with PVC'S or smooth muscle differentiated PVC'S or PCL cells and tissues reconstructed.

U.S. Pat. No. 7,452,532 by Alt and assigned to SciCoTec GmbH discloses a method for repairing tissue of a selected organ from among heart, brain, liver, pancreas, kidney, glands, and muscles in a patient's body. using cells that are intraluminally applied through a designated natural body vessel.

U.S. Pat. No. 7,078,232 by Konkle et al. discloses cells, methods and compositions based upon the use of cellular non-structural tissue-derived adult cells in the repair of articular cartilage fractures or defects and specifically treatment of articular cartilage fractures in a clinical setting.

U.S. Pat. No. 6,777,231 by Katz et al. describes perivascular cells and lattices. In one aspect, they provides a lipo-derived cell substantially free of pericytes and red blood cells and clonal populations of connective tissue cells.

Example 7

Protocol for the Therapeutic Use of Perivascular Cells (PVCs)

The present disclosure describes a method of treatment and a treatment protocol for treating various disease states using perivascular cell (PVC) therapy. The treatment method is used to treat a plurality of diseases and conditions. Each disease state and condition has a treatment protocol using the method of infusion to describe the method of treatment. The infusion method may be supplemented with a direct injection.

Injection provides a direct route within the structure. The cells are not subject to the pulmonary trap and lysing; therefore, provide a more direct effect to the structure injected and can signal surrounding protein cells to activate and assist in healing damaged or diseased tissue. On the other hand, infusion provides cytokine formation and release from the pulmonary tissue that circulate though out the body to affect damaged or diseased tissue though out the entire body. Additional cells which get through the pulmonary trap are attracted to damaged cells of the body where they lodge and influence local tissues to activate the healing responses.

The first step is to harvest capillary perivascular cells (CPVCs) from 80 mL of decanted cellular tissue, as detailed in Example 1. The cellular tissue can be processed for an autologous infusion or alternatively, can be from a donor either living or dead. The perivascular fraction (PVF) can be harvested prior to the infusion or prepared in advance and stored. Briefly CPVCs are separated by centrifugation. The supernatant oil layer is discarded after centrifuging and the buffy coat cell layer and cell pellet are collected. The buffy coats and cell pellets are mixed together and a small amount of saline is added. The mixture is filtered through a sterile cell filter and diluted with normal saline.

PVCs are diluted to 30 mL, divided into three (3) 10 mL aliquots and are ready for administration or storage. Any excess diluted PVCs are added to one aliquot which is designated to be a final aliquot.

A first aliquot is infused initially, a second aliquot is infused approximately 3 months after the initial infusion and a third final aliquot is infused approximately 6 months after the initial infusion.

The PVCs are diluted in normal saline to prepare tubes including 10 million to 100 million nucleated PVCs for the treatments described herein below, but preferably including 50 million to 100 million nucleated PVCs. 5-10 million nucleated cells per mL is the optimal target for the infusion protocol and is the preferable amount. 1-5 million nucleated cells per mL provide progress against the disease state, but the higher range is optimal.

After each infusion, follow-up testing and physician evaluation is required to monitor the effectiveness of the treatment and the patient's condition. The type of testing and evaluation vary according to the disease state under treatment, and are described in the following examples.

When the administered PVCs are isolated from a tissue obtained from an allogenic donor, one or more immunosuppressive agents are administered to the patient receiving the cells and/or tissue to reduce, and preferably prevent, rejection of the transplant. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways. Other examples include cyclosporin, myophenylate mofetil, rapamicin, and anti-thymocyte globulin.

Example 8

Use of Perivascular Cells (PVCs) for Cell Therapy

The standard procedure steps for the use of PVCs infusion for cell therapy requires a 20 or 22 gauge intravenous (IV) needle or a 16-25 gauge IV catheter; normal saline or another IV fluid and patient's vial(s) of PVCs isolated and prepared as described in Example 1.

The first step is the infusion of 500 ml bolus of normal saline (NS). Then the cells are mixed in 250 mls of NS and 125 mls of the NS/cellular mixture is infused in the patient over a 0-180 minute (ideally 45-60 minute) interval. A second infusion of 250 mls bolus of NS is performed prior to the infusion of the remaining 125mls of NS/cellular mixture over a 45 minute interval.

The treatment protocol may also include injections of the PVCs, along with infusions. In such alternatives, the protocol slightly varies depending on the number of treatments.

For single treatment, PVCs are isolated and prepared as disclosed in Example 1. A fractional amount of processed material is used for injection(s), and the remainder is used for cellular infusion. Material is fractionalized as needed for injection.

For multiple treatments, PVCs are isolated and prepared as disclosed in Example 1. A fractionalized amount of processed material is used for multiple injection(s) (as needed, and determined accordingly to disease state). The remaining processed material for multiple infusions and/or injections is fractionalized. The material that is not used is cryopreserve and thaw as needed to provide future multiple treatments with infusions and/or injections.

Example 9

Protocol for the Use of Perivascular Cells (PVCs) for the Treatment of Diabetes Mellitus For the treatment of a patient suffering from diabetes mellitus (Type 1 & 2 diabetes) with infusions of PVCs, the protocol described in Examples 7 and 8 is followed, with the administration of three infusions of diluted PVCs. As a non-limiting example, for the treatment of diabetes mellitus, a diabetic patient is advised to follow-up with his or her primary physician one week after the initial infusion and monthly thereafter for twelve months.

Three infusions, at 0, 3 months, 6 months are recommended. 80 mL decanted fat from harvest are diluted to 30 mL, and divided into 10 mL infusions (33% per infusion with any extra applied to first infusion).

In addition to the routine daily blood glucose measurements by the patient, HgbA1c and capillary blood glucose should be monitored by the physician.

Example 10

Protocol for the Use of Perivascular Cells (PVCs) for the Treatment of Chronic Obstructive Pulmonary Disease For the treatment of a patient suffering from chronic obstructive pulmonary disease with infusions of PVCs, the protocol described in Example 9 is followed, with the administration of three infusions of diluted PVCs. As a further non-limiting example, it is provided that chronic obstructive pulmonary disease includes, but is not limited to, emphysema, chronic bronchitis and asthma, for which the same protocol should be followed.

It is suggested that the patient follows-up with his or her primary physician one week after the initial infusion and three months thereafter for twelve months. Pulmonary function tests such as FEV1 (FEV1 is the volume of air that can forcibly be blown out in one second after full inspiration) are recommended.

Example 11

Protocol for the Use of Perivascular Cells (PVCs) for the Treatment of Traumatic Brain Injury In the case of traumatic brain injury, which comprises all types of injury and stress including post-traumatic stress syndrome, treatment with PVCs infusions follows the protocol outlined in Example 7. Cognitive function testing and brain scans should be performed prior to the first treatment and after twelve months.

It is suggested that the patient follows-up with his or her primary physician one month after the second infusion and starts occupational therapy two weeks after the third infusion if such therapy is indicated.

Example 12

Protocol for the Use of Perivascular Cells (PVCs) for the Treatment of Chronic Pain The treatment protocol for chronic pain which includes, but is not limited to, fibromyalgia, multi joint inflammatory arthritis, lupus, chemotherapy-induced peripheral neuropathy and other chronic inflammatory conditions, is the same as described in Example 9 with the following modifications.

The treatment begins with harvesting the cells and diluting the cells with normal saline. The nucleated PVCs are divided into three aliquots and administered initially and at three and six months after initial infusion. Prior to suspending an aliquot into 250 mL normal saline, a 1 mL diluted PVCs from the 10 mL aliquots is injected directly into a trigger point. No more than ten percent of each infusion aliquot may be used for trigger point injections. The remainder of the aliquot after the trigger point injection is infused according to the protocol in Example 7.

It is suggested that the patient follows-up with his or her primary physician one week after the initial infusion and three months thereafter for twelve months.

Example 13

Protocol for the Use of Perivascular Cells (PVCs) for the Treatment of Multiple Sclerosis The treatment protocol for multiple sclerosis starts with a larger amount of cellular tissue. The PVCs are harvested from 120 mL decanted cellular tissue. The harvested cells are diluted to 60 mL after filtering. The protocol described in Example 9 is followed with the following modifications.

In this protocol, the initial infusion comprises 20 mL of diluted PVCs suspended in normal saline. The first part of the protocol is an initial infusion with, followed by the infusion of 10 mL of diluted PVCs, suspended in 125 mL normal saline. A quick infusion of normal saline is then applied, followed by a second infusion of 10 mL of diluted PVCs suspended in 125 mL normal saline. After the initial infusion, infusions are administered at three weeks intervals for four subsequent infusions. Each subsequent infusion included an initial administration of normal saline, followed by the infusion of 5 mL of diluted PVCs suspended in normal saline. After a second infusion of normal saline, the remaining 5 mL of diluted CPVCs in normal saline are infused.

Cognitive exercises as described hereinabove are recommended to be performed by the patient during the infusion process. Follow-up post infusion includes evaluation with the primary physician, testing and physical therapy. Physician follow-up is recommended two weeks after the initial infusion and after 8 weeks after the last infusion. Physical therapy is recommended to start four weeks after the initial infusion or later when any pain has subsided sufficiently to allow exercise without much discomfort. Follow-up testing should include brain scans and cognitive evaluation.

This protocol can be modified in various ways, such as the initial collection may be 240 mL of decanted cellular tissue. The initial dilution of 60 mL of harvested cells may be a more concentrated bolus of 30 mL, with the initial infusion comprising 10 mL of the more concentrated cells followed by four subsequent infusions at three week intervals of 5 mL infusions, using the protocol as described in hereinabove.

The protocol may be repeated as needed for a total of ten infusions. Other inflammatory conditions, such as inflammatory bowel disease and chronic gastrointestinal conditions, may be treated following this protocol.

Example 14

Protocol for the Use of Perivascular Cells (PVCs) for the Treatment of Musculoskeletal Conditions For the treatment of musculoskeletal conditions with perivascular cells (PVCs), the protocol described in Example 7 is followed with the following modifications. This method of treatment is for musculoskeletal conditions such as osteoarthritis, rheumatoid arthritis, other rheumatic conditions and other conditions such as joint discomfort and other inflammatory conditions in the knee, ankle, hip, wrist and elbow as well as shoulder impingement syndrome, as non-limiting examples.

The amount of decanted cellular tissue from which the PVCs are harvested can vary from 40 mL to 65 mL depending on the number of joints that requires treatment. The harvested PVCs are diluted to 25 mL to 30 mL post filtering. Ten percent (10%) to thirty-three percent (33%) of the diluted CPVCs are injected directly into the joint. The remainder of the diluted CPVCs is suspended in saline and infused.

It should be noted that in the case of treatment of shoulder or hip conditions, intra-articular injections may require fluoroscopy and sedation according to the preference of the treating physician.

As a non-limiting example, in the case of a single joint injection, the amount of decanted cellular tissue from which the PVCs are harvested is 60 mL, which is diluted to 25 mL. 2.5 mL of the diluted PVCs are directly injected into a single joint (10% for injection) and the remaining 22.5 mL were suspended in 250 mL normal saline (90% for the infusion) and administered according to the protocol described in Examples 7 and 8.

In the case of injection treatment for two separate joints, 2.5 mL of the diluted PVCs (20% of total cells for injections) are directly injected into each of two joints and the remaining 20 mL (80% total cells for infusion) are suspended in 250 mL normal saline and administered according to the protocol previously described.

In the case of a multi-joint injection treatment, a larger volume of decanted cellular tissue is used, approximately 65 mL to produce 30 mL of diluted PVCs. The injection volume is reduced to 2 mL per injection, consuming one-third of the diluted PVCs. The maximum number of injections with this volume is five (33% of total cells for injections). Two-thirds or approximately 20 mL of the diluted CPVCs (67% of total cells for infusion) are suspended in 250 mL normal saline and infused using the treatment protocol illustrated in Examples 7 and 8.

In the case of joint injections, a single treatment is recommended.

Example 15

Protocol for the Use of Perivascular Cells (PVCs) for the Treatment of Neck and Back Pain Two treatments are recommended for the protocol for neck and back pain. Similarly to the other treatment protocols, PVCs are harvested from 80 mL decanted cellular tissue. The PVCs are diluted to 20 mL because only two treatments, the initial one and the second six (6) months later are recommended. The diluted PVCs are divided into two aliquots of 10 mL each, one aliquot for each treatment.

The diluted PVCs are injected into a trigger point, using 1 mL, which is approximately 10% (ten percent) of each aliquot. The remaining dilute PVCs are suspended in 250 mL of normal saline and are infused according to the treatment protocol described in Example 7.

Follow-up post infusion includes evaluation with the primary physician, testing and physical therapy. Physician follow-up is recommended two weeks after the initial infusion. Physical therapy is recommended to start two weeks after the initial infusion or later when any pain has subsided sufficiently to allow exercise without much discomfort and to continue as determined by the primary physician.

Example 16

Freezing and Thawing of Perivascular Cells (PVCs) Isolated From a Lipoaspirate If not administered after collection, isolated PVCs are frozen without the use of culture media. The volume of PVF cell suspension to be frozen is collected, the cell count in cells/ml and total number of cells are assessed. The previous cell count results can be used if counted less than 4 hours ago. The cell suspension should be frozen within an hour after collection or kept on ice for no more than 4 hours. The cell suspension is stored inside the isolator hood in a sterile environment. The cells are transferred to a 50 ml conical tube if not already in it, centrifuged at 3000 rpm for 6 min, and all liquid is decanted while leaving the pellet alone.

22-35 mls of the freezing agent is added to the pellet and the cells are mixed gently. Cryofreezing vials are labeled appropriately, and the cells are distributed in the amount needed per treatment guideline. The cryovials are moved out of the isolator hood, placed in a cryofreezing container except for the ones being injected/infused same day.

The cryofreezing container is placed in −80° C. freezer for at least for 4 hours. It is ok to leave the container in the −80° C. freezer overnight or longer. After 4 or more hours in −80° C., the vials containing cells are transferred to a long-term storage box in the freezer. The cells can also be transferred to a liquid nitrogen container. The cells can be stored at −80° C. for 6-12 months or in liquid nitrogen indefinitely.

Frozen vials can be thawed for quality control checks (viability and cell counted, one vial per batch of cells) or for cell use (administration to a patient). In both case, a water bath is heat to 37° C., tested, and ideally used for only one batch of cells tested at a time to better control the process. The vial(s) containing PVF cells is(are) took out of the freezer (or liquid nitrogen container) and immediately dipped in the 37° C. water bath until the vial is fully thawed.

If the thawing is intended for quality control only, the following steps do not need to be done inside the hood as no sterile processing is required, and only cell counting is performed.

If thawing is intended for cell use, the previous steps are followed, except that the cells are thawed in a sterile water bath or sterile saline bath. Once the cells are fully thawed, they were transferred to the final delivery system such as a syringe in a sterile manner, and used.

Depending on the protocol followed, the number of injections and/or infusions, various cryovials are prepared, as illustrated in Tables 5-7.

TABLE 5

Preparation of freezing vials for same day infusion/injection

| Protocol | Amount of Treatments | Amount of Cryofreezing Agent (ml) | # of Cryovials | # of Cryovials to Freeze | Same Day Vials to package (1st Infusion/Injection) |
| --- | --- | --- | --- | --- | --- |
| Protocol 1 Musculoskeletal Conditions (½ joint injections)*** | 1 | 25 | 6 | 0 | 6 |
| Musculoskeletal Conditions (Multiple Joint injections)* | 1 | 30 | 6 | 0 | 6 |
| Protocol 2 Diabetes, COPD, Traumatic Brain, Chronic Pain, Neck/Back Pain | 3 | 30 | 6 | 4 | 2 |
| Protocol 3 Multiple Sclerosis | 5 | 30 | 6 | 4 | 2 |

***1 Joint breakdown: 4 full vials and one vial with 2.5 ml for infusion; one vial with 2.5 ml for injection
***2 Joint breakdown: 4 full vials for infusion and 2 vials with 2.5 ml each for injections
*Multi-Joint breakdown: 2 full vials for injections and 4 vials for infusion

TABLE 6

Preparation of freezing vials for complete freezing (not same day)

| Protocol | Amount of Treatments | Amount of Cryofreezing Agent (ml) | # of Cryovials (Freeze all) |
| --- | --- | --- | --- |
| Protocol 1 Musculoskeletal Conditions (½ joint injections)*** | 1 | 25 | 6 |
| Musculoskeletal Conditions (Multiple Joint injections)* | 1 | 30 | 6 |
| Protocol 2 Diabetes, COPD, Traumatic Brain, Chronic Pain, Neck/Back Pain | 3 | 30 | 6 |
| Protocol 3 Multiple Sclerosis | 5 | 30 | 6 |

TABLE 7

Preparation of freezing vials for protocol with multiple injections

| Protocol | Tx 1 | Tx 2 | Tx 3 | Tx 4 | Tx 5 | # of Cryovials |
|---|---|---|---|---|---|---|
| Protocol 1<br>Musculoskeletal Conditions<br>(1/2 joint injections)*** | 6 | | | | | 6 |
| Musculoskeletal Conditions<br>(Multiple Joint injections)* | 6 | | | | | 6 |
| Protocol 2<br>Diabetes, COPD,<br>Traumatic Brain, Chronic<br>Pain, Neck/Back Pain | 2 | 2 | 2 | | | 6 |
| Protocol 3<br>Multiple Sclerosis | 2 | 1 | 1 | 1 | 1 | 6 |

***1 Joint breakdown: 4 full vials and one vial with 2.5 ml for infusion; one vial with 2.5 ml for injection
***2 Joint breakdown: 4 full vials for infusion and 2 vials with 2.5 ml each for injections
*Multi-Joint breakdown: 2 full vials for injections and 4 vials for infusion More or less infusions and/or injections can be found to have better desired results for any given disease or condition as time continues and studies are performed. Those reflect the number of infusions and/or injections that are currently used.

Example 17

Automated System for Separating and Concentrating Perivascular Cells (PVCs) From a Cellular Non-Structural Tissue An automated system is developed to isolate and concentrate perivascular cells (PVCs) from a cellular non-structural tissue.

Such system for separating and concentrating cells from cellular non-structural tissue includes one or more collection chambers, a processing chamber, a waste chamber, an output chamber and a sample chamber. The various chambers are connected to one another via one or more conduits such that fluids containing biological material may pass from one chamber to another in a closed, or functionally closed, sterile fluid/tissue pathway which minimizes exposure of tissue, cells, biologic and non-biologic materials to contaminants. The waste chamber, the output chamber and the sample chamber are optional. The system contained clinically irrelevant quantities of endotoxin. The system also includes a plurality of filters. The filters are effective to separate the cells and/or progenitor cells from, among other things, collagen, free lipids, pericyte, that may be present in the solution after ultrasonic cavitation of the cellular non-structural tissue sample.

The filter assembly may include a hollow fiber filtration device and a percolative filtration device, which may or may not be used with a sedimentation process. The filter assembly may also comprise a centrifugation device, which may or may not be used with an elutriation device and process. The system may comprise a combination of these filtering devices. The filtration functions can be two-fold, with some filters removing things from the final concentration such as collagen, free lipid, and with other filters being used to concentrate and cleanse the final product.

One or more components of the system are automated and include an internal processing device and associated software programs which control many of the processing functions. Components of the system may be disposable, such that portions of the system can be disposed of after a single use. Such a system also comprises a re-usable component which includes the processing device (computer and associated software programs) and other components such as motors, pumps, etc.

Although the invention has been described with reference to the above examples, it will be understood that modifications and variations are encompassed within the spirit and scope of the invention. Accordingly, the invention is limited only by the following claims.

What is claimed is:

1. A method of isolating a perivascular cells (PVCs) from a cellular non-structural tissue comprising:
    a) indirectly sonicating the cellular non-structural tissue with an ultrasonic cavitation head in a closed and sterile system; and
    b) collecting the PVCs,
wherein the ultrasonic cavitation head and cellular non-structural tissue are located in distinct containers, thereby isolating a PVCs without lysing or exploding PVCs.

2. The method of claim 1, wherein the PVCs comprise pericytes.

3. The method of claim 1, wherein the distance between the tissue and the ultrasonic cavitation head is about 0.1-20 millimeters.

4. The method of claim 3, wherein the distance between the tissue and the ultrasonic cavitation head is about 3-4 millimeters.

5. The method of claim 1, wherein the tissue is sonicated from about 1 minute to about 9 hours.

6. The method of claim 5, wherein the tissue is sonicated for about 5-15 minutes.

7. The method of claim 1, wherein the sonication is performed at about 15-50 kHz.

8. The method of claim 1, wherein the cellular non-structural tissue is human.

9. The method of claim 1, wherein the cellular non-structural tissue is obtained by surgical excision or aspiration.

10. The method of claim 1, further comprising differentiating the PVCs.

* * * * *